United States Patent
Schmidt

(10) Patent No.: US 11,791,022 B2
(45) Date of Patent: Oct. 17, 2023

(54) CROSS DISCIPLINE DISEASE MANAGEMENT SYSTEM

(71) Applicant: Beckman Coulter, Inc., Brea, CA (US)

(72) Inventor: Carola Schmidt, Henstedt-Ulzburg (DE)

(73) Assignee: Beckman Coulter, Inc., Brea, CA (US)

( * ) Notice: Subject to any disclaimer, the term of this patent is extended or adjusted under 35 U.S.C. 154(b) by 384 days.

(21) Appl. No.: 16/488,503

(22) PCT Filed: Feb. 28, 2018

(86) PCT No.: PCT/US2018/020087
§ 371 (c)(1),
(2) Date: Aug. 23, 2019

(87) PCT Pub. No.: WO2018/160619
PCT Pub. Date: Sep. 7, 2018

(65) Prior Publication Data
US 2020/0243171 A1    Jul. 30, 2020

Related U.S. Application Data

(60) Provisional application No. 62/464,631, filed on Feb. 28, 2017.

(51) Int. Cl.
*G16H 10/40* (2018.01)
*G16H 40/67* (2018.01)
(Continued)

(52) U.S. Cl.
CPC .............. *G16H 10/40* (2018.01); *G16H 10/60* (2018.01); *G16H 40/67* (2018.01); *G16H 50/20* (2018.01)

(58) Field of Classification Search
CPC ......... G16H 10/40; G16H 10/60; G16H 50/20
(Continued)

(56) References Cited

U.S. PATENT DOCUMENTS

| 5,125,737 A | 6/1992 | Rodriguez et al. |
| 5,529,933 A | 6/1996 | Young et al. |

(Continued)

FOREIGN PATENT DOCUMENTS

| EP | 1021701 | 7/2000 |
| EP | 1718966 | 11/2006 |

(Continued)

OTHER PUBLICATIONS

"BIOMARKER," The Pharmaceutical Society of Japan, a pharmaceutical science glossary, 2008, 2 pgs.
(Continued)

*Primary Examiner* — John R Downey
(74) *Attorney, Agent, or Firm* — Frost Brown Todd LLP

(57) ABSTRACT

A middleware device or software may be placed in communication with one or more testing instruments and a lab information system. As samples are collected from patients and tested with the testing instruments, test results pass through the middleware and are analyzed in context with other data, such as patient history, testing instrument history, and test results from other tests of the sample, in order to determine whether a particular result is acceptable, whether retesting is needed, whether additional sample collection or testing is needed, and whether currently ordered testing is still necessary. When the middleware determines a need for additional testing or retesting it may automatically create orders for such testing in order to reduce delays in manual review of testing results.

20 Claims, 6 Drawing Sheets

(51) Int. Cl.
*G16H 10/60* (2018.01)
*G16H 50/20* (2018.01)

(58) Field of Classification Search
USPC .................................. 705/2, 3; 600/300, 301
See application file for complete search history.

(56) References Cited

U.S. PATENT DOCUMENTS

| | | | |
|---|---|---|---|
| 6,228,652 B1 | 5/2001 | Rodriquez et al. | |
| 7,109,036 B2 | 9/2006 | Ortiz et al. | |
| 7,135,341 B2 | 11/2006 | Ortiz et al. | |
| 7,176,031 B2 | 2/2007 | Li et al. | |
| 7,195,919 B2 | 3/2007 | Jacobs et al. | |
| 7,285,417 B2 | 10/2007 | Ortiz et al. | |
| 7,390,662 B2 | 6/2008 | Riley et al. | |
| 7,393,688 B2 | 7/2008 | Ortiz et al. | |
| 8,094,299 B2 | 1/2012 | Wells et al. | |
| 8,189,187 B2 | 5/2012 | Graham et al. | |
| 8,221,995 B2 | 7/2012 | Lee et al. | |
| 8,719,053 B2* | 5/2014 | Showalter | G16H 40/40 705/3 |
| 9,939,453 B2 | 4/2018 | Lu et al. | |
| 10,221,453 B2 | 3/2019 | Shi et al. | |
| 2001/0051879 A1 | 12/2001 | Johnson et al. | |
| 2001/0051880 A1 | 12/2001 | Schurenberg et al. | |
| 2003/0105648 A1 | 6/2003 | Schurenberg et al. | |
| 2004/0042471 A1* | 3/2004 | Yung | G05B 15/02 370/401 |
| 2004/0220761 A1* | 11/2004 | Yundt-Pacheco | G16H 10/40 702/84 |
| 2004/0267562 A1* | 12/2004 | Fuhrer | G16H 10/40 235/375 |
| 2005/0022103 A1* | 1/2005 | Yundt-Pacheco | G16H 10/40 715/273 |
| 2005/0159982 A1* | 7/2005 | Showalter | G16H 10/40 705/2 |
| 2006/0159325 A1* | 7/2006 | Zeineh | G16H 10/20 382/128 |
| 2008/0186134 A1* | 8/2008 | Parkhurst | G16H 10/40 340/5.8 |
| 2009/0149724 A1 | 6/2009 | Mark et al. | |
| 2011/0046910 A1* | 2/2011 | Haas | G01N 35/00871 702/108 |
| 2011/0076685 A1 | 3/2011 | Moeller et al. | |
| 2011/0166794 A1 | 7/2011 | Linssen et al. | |
| 2012/0109531 A1* | 5/2012 | Knafel | G05B 19/41865 702/19 |
| 2012/0109682 A1* | 5/2012 | Seltzer | G16Z 99/00 705/2 |
| 2013/0197943 A1* | 8/2013 | Conlin | G16H 10/40 705/3 |
| 2013/0246079 A1* | 9/2013 | Hoffman | G16H 40/63 705/2 |
| 2014/0084930 A1 | 6/2014 | Han | |
| 2015/0338427 A1* | 11/2015 | Pollack | G01N 35/0095 422/67 |
| 2016/0356801 A1* | 12/2016 | Glavina | G01N 35/0092 |
| 2018/0285153 A1* | 10/2018 | Yu | G16H 50/20 |
| 2019/0128906 A1 | 5/2019 | Ramirez et al. | |
| 2019/0324035 A1 | 10/2019 | Magari et al. | |
| 2019/0324036 A1 | 10/2019 | Xin et al. | |
| 2019/0348182 A1 | 11/2019 | Magari et al. | |
| 2019/0362824 A1 | 11/2019 | Xin et al. | |
| 2019/0383800 A1 | 12/2019 | Careaga et al. | |
| 2021/0007675 A1 | 1/2021 | Tejidor et al. | |
| 2021/0010924 A1 | 1/2021 | Tejidor et al. | |
| 2021/0011005 A1 | 1/2021 | Tejidor et al. | |

FOREIGN PATENT DOCUMENTS

| | | |
|---|---|---|
| WO | WO 88/07198 A1 | 9/1988 |
| WO | WO 2004/044556 A2 | 5/2004 |
| WO | WO 2012/139047 A2 | 10/2012 |
| WO | WO 2014/028534 A2 | 2/2014 |
| WO | WO 2014/084930 | 6/2014 |
| WO | WO 2014/154810 A1 | 10/2014 |
| WO | WO 2017/132132 | 8/2017 |
| WO | WO 2019/028448 A1 | 2/2019 |

OTHER PUBLICATIONS

"Red Blood Cell Distribution With (RDW): Definition and Calculation—LabCE.com, Laboratory Continuing Education," Nov. 2012, downloaded Aug. 22, 2019 from: https://labce.com/spg579122_red_blood_cell_distribution_width_rdw_definition_a.aspx, 1 pg.

Sukhacheva, et al., "The Role of Monocytes in the Progression of Sepsis," Beckman Coulter, 2018, downloaded Aug. 22, 2019 from: media.beckmancoulter.com/-/media/diagnostics/products/hematology/early-sepsis-indicator/docs/role-of-monocytes-for-progression-of-sepsis-en.pdf, 12 pgs.

Zhou, et al., "VCS parameters of neutrophils, monocytes and lymphocytes may indicate local bacterial infection in cancer patients who accepted cytotoxic chemotherapeutics," Eur J Clin Microbiol Infect Dis, 2016, 35:41-48, 8 pgs.

Zonneveld, R., et al., "Analyzing Neutrophil Morphology, Mechanics, and Motility in Sepsis: Options and Challenges for Novel Bedside Technologies," Crit Care Med, 2016, 44(1):218-228, 11 pgs.

European Examination Report dated Oct. 15, 2020 for Application No. EP 17704357.7, 10 pgs.

International Search Report and Written Opinion dated Aug. 23, 2019 for International Application No. PCT/US2019/028488, 10 pgs.

International Search Report and Written Opinion dated Oct. 20, 2020 for International Application No. PCT/US2020/041535, 12 pgs.

International Search Report and Written Opinion dated Oct. 8, 2020 for International Application No. PCT/US2020/041548, 10 pgs.

International Search Report and Written Opinion dated Oct. 5, 2020 for International Application No. PCT/US2020/041541, 10 pgs.

Japanese Office Action, Notice of Reasons for Refusal, dated Oct. 29, 2020 JP 2018-538892, 27 pgs.

U.S. Office Action, Restriction Requirement, dated Apr. 7, 2021 for U.S. Appl. No. 15/987,541, 5 pgs.

U.S. Office Action, Non-Final Rejection, dated Jul. 31, 2020 for U.S. Appl. No. 16/073,757, 23 pgs.

U.S. Office Action, Notice of Allowance, dated Feb. 8, 2021 for U.S. Appl. No. 16/073,757, 20 pgs.

Aird, William C., "The Hematologic System as a Marker of Organ Dysfunction in Sepsis", Mayo Clin Proc., Jul. 2003;78:869-881, 2003 Mayo Foundation for Medical Education and Research.

Anonymous, "Multiple Logistic Regression Analysis", Jan. 17, 2013, retrieved from http://sphweb.bumc.cu.edu/otlt/MPH-Modules/BS/BS704_Multivariable/BS704_Multivariables8.html.

Bhargava, et al. "Elevated mean neutrophil volume+ CRP is a highly sensitive and specific predictor of neonatal sepsis", Letter to the Editor, International Journal of Laboratory Hematology, DOI: 10.1111/iijh.12120, 2013, 4 pages.

Celik, et al., "Automated determination of neutrophil VCS parameters in diagnosis and treatment efficacy of neonatal sepsis", Pediatric Research, vol. 71, No. 1, Jan. 2012, pp. 121-125.

Chaves, et al. "Neutrophil Volume Distribution Width: A New Automated Hematologic Parameter for Acute Infection", Arch Pathol Lab Med, vol. 130. Mar. 2006, pp. 378-380.

Chaves, et al. Quantitative Determination of Neutrophil VCS Parameters by the Coulter Automated Hematology Analyzer: New and Reliable Indicators for Acute Bacterial Infection. American Journal Clinical Pathology, 2005, 124:440-444.

Cho, et al., "Biomarkers of Sepsis", Infection & Chemotherapy, Feb. 2014; 46:1-12.

Crouser, et al., "Improved Early Detection of Sepsis in the ED with a Novel Monocyte Distribution Width Biomarker", 152#3 CHEST, Sep. 2017, pp. 518-526.

(56) References Cited

OTHER PUBLICATIONS

Dellinger, et. al. "Surviving Sepsis Campaign: International Guidelines for Management of Severe Sepsis and Septic Shock, 2012", Intensive Care Medicine, 2013, 39:164-228.

Dilmoula, et al., "Volume, Conductivity and Scatter Properties of Leukocytes (VCS Technology) in Detecting Sepsis in Critically Ill Adult Patients", Blood (ASH annual Meeting Abstracts) 2011; 118: Abstract 4729, 3 pages.

Early Sepsis Indicator Application Addendum UniCel DxH 900 Coulter Cellular Analysis System, Beckman Coulter, published Version: v1, Available online at: https://www.analis.be/site/objects/media/0/0/8/1/9/0081990_media/media1.pdf, Apr. 26, 2018, 38 pages.

Ferrer, et al., "Emperic Antibiotic Treatment Reduces Mortality in Severe Sepsis and Septic Shock from the First Hour: Results from a Guideline-Based Performance Improvement Program", Critical Care Medicine, Aug. 2014, vol. 42, No. 8, pp. 1749-1755.

Gaieski, et al., "Impact of time to antibiotics on survival in patients with severe sepsis or septic shock in whom early goal-directed therapy was initiated in the emergency department", Critical Care Medicine, 2010, vol. 38, No. 4, pp. 1045-1053.

Garnacho-Montero, et al., "Impact of adequate empirical antibiotic therapy on the outcome of patients admitted to the intensive care unit with sepsis", Critical Care Medicine, 2003:31 :2742-51.

Gea-Banecloche, et al. "Sepsis associated with immunosuppressive medications: An evidence-based review" Critical Care Medicine 2004; 32:S578-S590.

Glickman, et al., Disease Progression in Hemodynamically Stable Patients Presenting to the Emergency Department with Sepsis. Academic Emergency Medicine, vol. 17, Issue 4, Apr. 2, 2010, pp. 383-390.

Goyette, et al., "Hematologic changes in sepsis and their therapeutic implications," Seminars in Respiratory and Critical Care Medicine, vol. 25, No. 6, pp. 645-659 (2004).

Hou, et al., "Viral infection triggers rapid differentiation of human blood monocytes into dendritic cells", Blood, Mar. 29, 2012, vol. 119, No. 12, pp. 3128-3132.

Kaukonen, et al., "Systemic Inflammatory Response Syndrome Criteria in Defining Severe Sepsis," New England Journal of Medicine, 372: 1629-38, Apr. 23, 2015, (doi:610.1056/NEJMoal415236).

Lee, et al., "Mean cell volumes of neutrophils and monocytes are promising markers of sepsis in elderly patients", Blood Research, vol. 48, No. 3, Sep. 2013, 5 pages.

Levy, et al., "2001 SCCM/ESICM/ACCP/ATS/SIS Sepsis Definitions Conference", Critical Care Medicine, Mar. 28, 2003, 29: 530-538.

Liu, et al., "Hospital Deaths in Patients with Sepsis from 2 Independent Cohorts", JAMA Jul. 2, 2014; 312: 90-92.

Mardi, et al., Mean cell volume of neutrophils and monocytes compared with C-reactive protein, interleukin-6 and white blood cell count for prediction of sepsis and nonsystemic bacterial infections, accepted for publication, Sep. 23, 2009, International Journal of Laboratory Hematology 2010;32:410-418.

Park, et al., "Screening of sepsis using leukocyte cell population data from the Coulter automatic blood cell analyzer DxH800", International Journal of Laboratory Hematology, Dec. 6, 2010, 9 pages.

Raimondi, et al., "Automated Determination of Neutrophil Volume as Screening Test for Late-Onset Sepsis in Very Low Birth Infants", Pediatric Infectious Disease Journal, Feb. 2010; 29:288-89.

Seymour, et al. "Severe Sepsis in Pre-Hospital Emergency Care: Analysis of Incidence, Care, and Outcome", American Journal of Respiratory Critical Care Medicine, Dec. 15, 2012; 186:1264-71.

Shalova, et al., "Human Monocytes Undergo Functional Reprogramming during Sepsis Mediated by Hypozia-Inducible Factor-1a", Immunity, Mar. 17, 2015; 42:484-98.

Singer, et al., "The Third International Consensus Definitions for Sepsis and Septic Shock (Sepsis-3)," JAMA, 10 315(8): 801-810, Feb. 23, 2016.

Skibsted, et al., "Bench-to-bedside review: Future novel diagnostics for sepsis- a systems biology approach", Critical Care Oct. 4, 2013;17:231, 15 pages.

Torio, et al., "National Inpatient Hospital Costs: The Most Expensive Conditions by Payer, 2011", H-CUP US, Aug. 2013, 8 pages, retrieved from: https://www.hcup-us.ahrq.gov/reports/statbriefs/sb160.jsp.

"UniCel DxH 800—Coulter Cellular Analysis System", Available online at: https://www.udh.med.sa/advices/DxH_operator_Manual.pdf, Aug. 5, 2017, 54 pages.

Vis, et al., "Verification and Quality Control of Routine Hematology Analyzers", International Journal of Laboratory Hematology, vol. 38, No. 1, May 9, 2016, pp. 100-109.

Warner, "Tips for evaluating a peripheral blood smear for possible sepsis," Jan. 15, 2013, 3 pages, available at laboratorian.advanceweb.com/signs-of-sepsis/.

International Search Report and Written Opinion dated Apr. 20, 2017 for International Application No. PCT/US2017/014708, 16 pages.

International Search Report and Written Opinion dated May 4, 2018 for International Application No. PCT/US2018/020087, 13 pages.

International Search Report and Written Opinion dated Mar. 26, 2019 for International Application No. PCT/US2018/057645, 16 pages.

International Search Report and Written Opinion dated Aug. 2, 2019 for International Application No. PCT/US2019/028487, 7 pages.

International Search Report and Written Opinion dated Aug. 20, 2019 for International Application No. PCT/US2019/031151, 9 pages.

International Search Report and Written Opinion dated Sep. 4, 2019 for International Application No. PCT/US2019/028486, 11 pages.

European Office Action dated Aug. 9, 2022 for Application No. 18712041.5, 6 pages.

\* cited by examiner

CROSS DISCIPLINE DISEASE MANAGEMENT SYSTEM

This application is a National Stage Entry of PCT Application No. PCT/US18/20087, entitled "Cross Discipline Disease Management System," filed Feb. 28, 2018, which claims priority to U.S. Provisional Application No. 62/464,631, entitled "Cross Discipline Disease Management System," filed Feb. 28, 2017, the disclosures of which are incorporated by reference herein.

FIELD

The disclosed technology pertains to a system for managing collection and testing of samples from a patient during medical treatment and/or monitoring.

BACKGROUND

Diagnosis and treatment of medical conditions often involves the collection and analysis of biological samples, such as blood or tissue, from a patient. Multiple samples may be gathered from a patient upon admittance, or may be gathered over time and as clinicians determine that they are needed. With a wide variety of samples being gathered from any single person, some estimates indicate that a sample set can generate as many as 80 or even more sets of test results. Results may be generated from specialized equipment that is needed to test each sample, and samples may be separately tested by one of many lab technicians (or even at multiple labs) for certain characteristics. While such specialization of equipment and personnel allows for improved testing results, it often comes at the cost of compartmentalization of knowledge which can interfere with or delay the holistic consideration of information regarding a patient's health.

For example, two technicians may test samples from the same patient or separately determine results that, when viewed together, indicate that the patient does or does not have a serious medical condition (or does or does not have a predisposition for developing a condition, such as diabetes, in the future). In conventional laboratory information systems ("LIS") and hospital information systems ("HIS") those results can often slowly trickle through various systems and levels of manual review until, sometimes later, they both become available and viewable to a person that has the expertise to interpret them in a holistic manner. As a result, valuable time can be lost in diagnosing and treating the patient.

Additionally, certain results in prior tests or combinations of tests often give rise to a need for retesting of samples and additional testing of samples. For example, a certain result of a sample test may be known to indicate either a rare and serious medical condition, or a poorly preserved or untimely delivered sample. In such cases, it may be desirable to compare the results of a test performed with one sample of material from a patient with tests performed on other materials from that same individual in order to distinguish between results reflecting serious medical conditions and results reflecting issues with preservation or delivery of a sample. However, with conventional approaches, it would not be possible for this type of cross test comparison to take place, or for the need for reflex testing to be identified, until after all test results had been assembled and manually considered at an LIS.

SUMMARY

There may therefore be a need for an improved system for managing and reacting to results of sample testing in a fast, efficient and comprehensive manner. It may thus be an object of some embodiments to provide an improved system for managing and reacting to results of sample testing in a fast, efficient and comprehensive manner. As described previously, often the first place to see all results from tests of different body fluids (called a "consolidated patient result") will be at the LIS level. Due to different measurement test procedures and measurement times, if an add on order (e.g., reflex testing) is necessary it can be highly beneficial to detect such necessity early to avoid sample aging. Accordingly, in some embodiments, a role based intelligence at a middleware level may automatically speed up response time and reduce sample aging in a manual, semi-automated, or fully automated process laboratory environment. In some embodiments, this objective may be fulfilled by the subject-matter of the independent claims, wherein further embodiments are incorporated in the dependent claims.

BRIEF DESCRIPTION OF THE DRAWINGS

The drawings and detailed description that follow are intended to be merely illustrative and are not intended to limit the scope of the invention as contemplated by the inventors.

DETAILED DESCRIPTION

Figure 1:
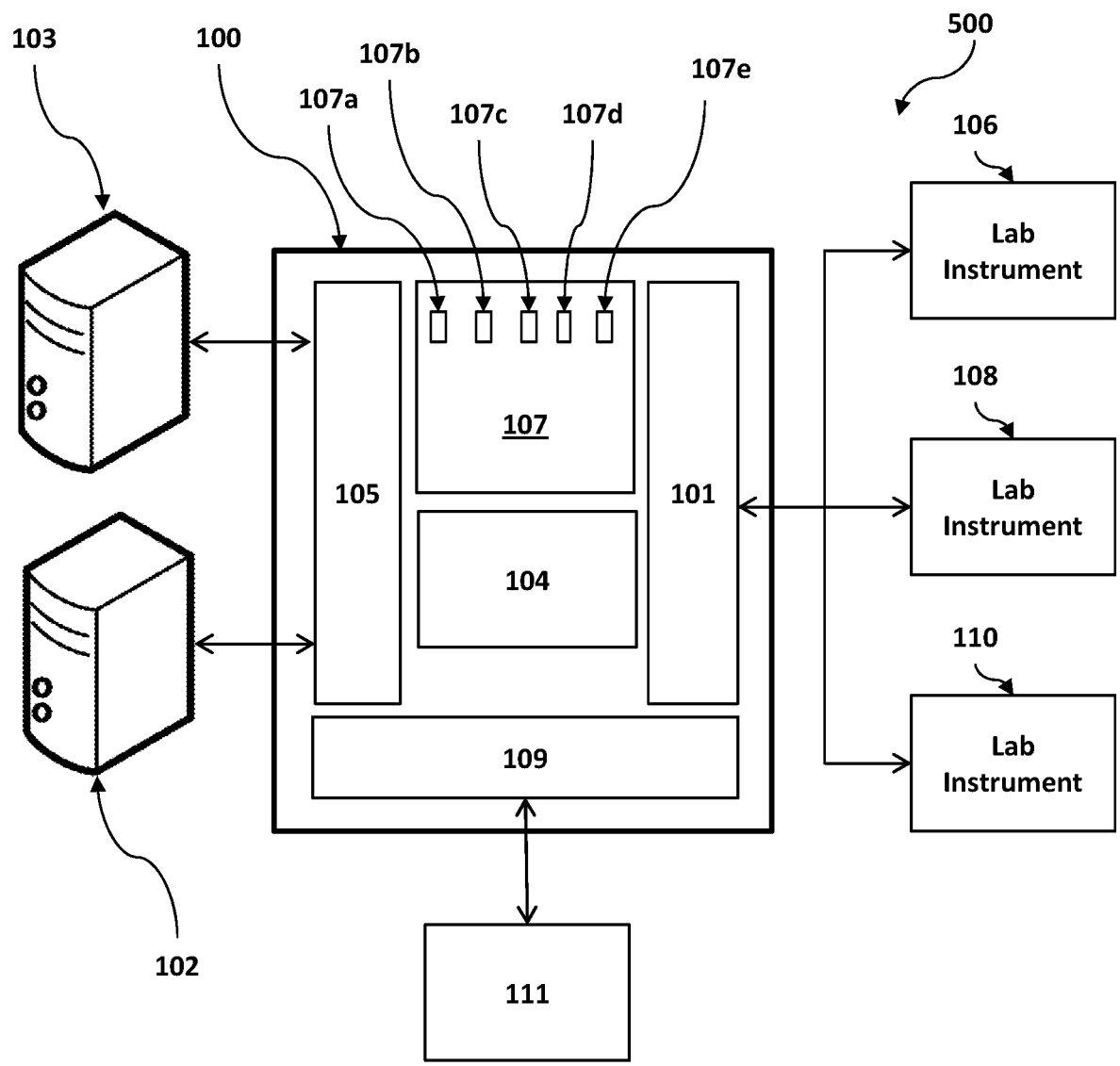
FIG. 1 is a schematic diagram of an exemplary cross-discipline system for managing medical testing and/or an exemplary information system for managing medical testing.

The inventor has conceived of novel technology that, for the purpose of illustration, is disclosed herein as applied in the context of the management of data from medical test results. While the disclosed applications of the inventor's technology satisfy a long-felt but unmet need in the art of management of data from medical test results, it should be understood that the inventor's technology is not limited to being implemented in the precise manners set forth herein, but could be implemented in other manners without undue experimentation by those of ordinary skill in the art in light of this disclosure. Accordingly, the examples set forth herein should be understood as being illustrative only, and should not be treated as limiting.

According to a first aspect, an information system for managing medical testing may be provided. Such an information system may comprise a computing server configured to exchange information with at least one external laboratory instrument and at least one external patient data information system. Such an information system may further comprise an instrument communication interface communicatively coupled with the computing server and may be configured to provide and/or establish a data communication between the computing server and the at least one external laboratory instrument. Such an information system may further comprise an information system interface communicatively coupled with the computing server and configured to provide and/or establish a further data communication between the computing server and the at least one external patient data information system, wherein the at least one external patient data information system may be configured to maintain and/or maintains a patient data set comprising at least one of a set of test orders and a history data set. In some embodiments, a computing server of the information system may comprise a first receiving section configured to receive an instrument data set from the at least one external laboratory instrument via the instrument communication interface. In some embodiments, a computing server of the information system may further comprise a second receiving section configured to receive a history data set from the at least one external patient data information system via the information system interface. In some embodiments, a computing server may further comprise a test management section configured to build and/or generate a test management data set based on the instrument data set received from the at least one external laboratory instrument and based on the history data set received from the at least one external patient data information system. In some embodiments, a computing server of an information system may further comprise a rules engine and/or a rules section configured to apply a set of test management rules to the test management data set to generate a testing task. Accordingly, in some embodiments, a rules engine and/or computing server may be configured to generate a testing task based on applying the set of test management rules to the test management data set. In some embodiments, a computing server of an information system may further comprise an updating section configured to update a set of test orders of a patient data set maintained by the at least one external patient data information system based upon the testing task. In some embodiments, an updating section and/or a computing server may be configured to provide an update information and/or update data associated with the testing task to the at least one external patient data information system, e.g. via the information system interface. Therein, the instrument data set may comprise test results associated with a patient, and the history data set may comprise at least one of biographical and historical information associated with the patient.

Generally, in some embodiments, an information system may be configured to manage data and/or react to test results from one or more laboratory instruments and/or the at least one external patient data information system. By way of example, in some embodiments, the information system may refer to a middleware hub as described in detail with reference to the attached drawings. Further, in some embodiments an information system may be a centralized system, in which all functions may be performed at one location. Alternatively, in some embodiments, the information system may be a de-centralized system, in which different functions may be performed at different locations. By way of example, an information system may reside in a cloud computing environment and/or the information system may comprise one or more servers in one or more data networks. Therein, each server may refer to a collection of servers. Alternatively, the information system may be a standalone computing device. The information system may be at least partly embedded in one or more software modules, which may be executed and/or running one or more separate devices, such as e.g. a laboratory information system (LIS) and/or a hospital information system (HIS).

In some embodiments, an instrument communication interface may comprise a hardware component and/or a software component enabling the computing server of the information system to establish the data communication between the computing server and the at least one external laboratory instrument. Such an instrument communication interface may enable the computing server to communicate with the at least one external laboratory instrument. Accordingly, in some embodiments, the instrument communication interface may comprise appropriate hardware means, such as e.g. a physical interface, for connecting a computing server to at least one external laboratory instrument and/or to a common data network, for exchanging information and/or for exchanging data. Alternatively or additionally, an instrument communication interface may comprise software means, such as e.g. an appropriate data protocol section, for exchanging information and/or for exchanging data using a certain data protocol for data transfer. Therein, the data communication provided by the instrument communication interface may refer to a wireless and/or a tethered data communication.

Similarly, in some embodiments an information system interface may comprise a hardware component and/or a software component enabling the computing server of the information system to establish the further data communication between the computing server and the at least one external patient data information system. The information system interface may enable the computing server to communicate with the at least one external patient data information system. Accordingly, the information system interface may comprise appropriate hardware means, such as e.g. a physical interface, for connecting the computing server to the at least one external patient data information system and/or to a common data network, for exchanging information and/or for exchanging data. Alternatively or additionally, the information system interface may comprise software means, such as e.g. an appropriate data protocol section, for exchanging information and/or for exchanging data using a certain data protocol. Therein, the further data communication provided by the information system interface may refer to a wireless and/or a tethered data communication.

In some embodiments, the instrument communication interface and the information system interface may both be embedded and/or may both be part of an interface arrangement of the information system. In other words, the information system may comprise an interface arrangement for providing the data communication between the computing server and the at least one external laboratory instrument as well as for providing the further data communication between the computing server and the at least one external patient data information system.

In some embodiments, the computing server may generally refer to a computing device, a computing circuitry, a processing device, and/or a processing circuitry. However, the computing server may also refer to a plurality of computing devices. Features, functions, characteristics, functionalities and/or functional modules of the computing server may be at least partly embedded in software modules. Particularly, in some embodiments, a first receiving section, a second receiving section, a test management section, a rules engine and/or an updating section of the computing server may refer to functional modules of the computing server. One or more of these functional modules, i.e. one or more of the first receiving section, the second receiving section, the test management section, the rules engine and/or the updating section, may at least partly be implemented as programmed software modules or procedures, respectively. However, any of these functional modules may be implemented fully or partially in hardware.

The external laboratory instrument may refer to any device for testing and/or analyzing a sample of a patient, such as e.g. a bodily fluid sample and/or a tissue sample of a patient. Therein, the term "external" may indicate that the laboratory instrument may not necessarily be part of the information system. The external laboratory instrument may be part of and/or may be connected to a laboratory information system (LIS), e.g. via an appropriate data network.

Further, the external patient data system may refer to any device configured to maintain a patient data set. Therein, the term "external" may indicate that the patient data system may not necessarily be part of the information system. By way of example, the external patient data system may be part of and/or may be connected to a LIS and/or a hospital information system (HIS), e.g., via an appropriate data network.

In some embodiments, the patient data set may comprise a set of test orders and a history data set of a patient. Therein, the history data set may comprise at least one of biographical and historical data associated with and/or relating to a patient. Accordingly, in some embodiments a history data set and/or a biographical information of the history data set may comprise data relating to and/or associated with physical characteristics of a patient, such as e.g. a height, a weight, an age, and/or a gender of a patient. Further, in some embodiments, a history data set and/or historical information of the history data set may comprise data relating to and/or associated with a past medical history of a patient, such as e.g., previous diagnoses and/or procedures, as well as other information describing the medical history of the patient, such as e.g. diseases, prescriptions and/or allergies of a patient. Further, in some embodiments a set of test orders of a patient data set may comprise data relating to and/or associated with any test performed on any sample of a patient, e.g., currently, in the past, and/or in the future. In some embodiments, a set of test orders may further comprise data relating to and/or associated with, e.g., a chronology of samples gathered from the patient and/or procedures performed on the patient.

In some embodiments, an instrument data set may comprise test results associated with a patient and/or with a sample of the patient. The instrument data set and/or the test results may, for example, comprise data relating to and/or associated with at least one of an identification of a sample, a sample type, a type of a test performed on a sample, a numerical test result, any custom notes relating to a specific test, an identification of a laboratory instrument, an identification of a reagent used for testing, and any data output by a laboratory instrument. Moreover, in some embodiments, an instrument data set may comprise data relating to and/or associated with e.g. an identification of a laboratory instrument, a location of a laboratory instrument, personnel having access to a laboratory instrument, a model of a laboratory instrument, a serial number of a laboratory instrument, a manufacturer of a laboratory instrument, a software version of a laboratory instrument, a hardware version of a laboratory instrument, maintenance dates of a laboratory instrument, and/or calibration records of a laboratory instrument.

The test management data set may generally refer to a comprehensive, combined and/or merged data set comprising and/or associated with the instrument data set and the history data set. Thus, in some embodiments, a test management data set may contain any information and/or data available for a specific patient, which may be relevant for diagnosis and/or therapy (analysis). Therefore, in some embodiments generating and/or building the test management data set may allow to provide a comprehensive data set, which in turn allows a comprehensive analysis of a patient's disease and/or an analysis of further steps to be taken in diagnosis and/or therapy (analysis). The test management data set may comprise data relating to and/or associated with test results of present, past and/or future procedures. Also, the test management data set may comprise data and/or information relating to laboratory instruments, which may be used to perform procedures and/or to perform sample collection.

In some embodiments, a test management data set may be provided as input to the rules engine for applying the test management rules. In some embodiments, a rules engine may be configured to implement the test management rules and/or to evaluate the test management data set by applying the test management rules. In some embodiments, by applying the test management rules to the test management data set, the information system may determine e.g. if a retest is required, if an additional test is required, if a presently ordered test should be modified and/or if a presently ordered test should be canceled.

In some embodiments, test management rules may be applied to the test management data set by means of the rules engine may e.g. be a set of Boolean rules for examining and/or evaluating the test management data set in terms of certain occurrences. Such occurrences may for instance relate to an improper age, an improper storage of a sample, a specific characteristic of a sample test, a specific result of a sample test. In some embodiments, application of each of the test management rules to the test management data set may result in a value of the respective test management rule. By way of example, each of the test management rules may be evaluated to a true or a false value. In some cases, evaluating a single test management rule as true or false may indicate that the test result was not acceptable, e.g. due to an inaccurate test result. In other cases, a plurality of evaluations of a plurality of test management rules as true or false may indicate that the test result was not acceptable. By way of example, in some embodiments a rules engine and/or the computing server may determine by applying the test management rules to the test management data set that a sample was too old when it was tested and that the sample had been stored inappropriately before testing. Accordingly, in some embodiments, it may be determined by the information system that a corresponding test result may not be acceptable.

Generally, the term "testing task" may refer to at least one of a new test order, a new test order and a new sample order, a test order modification, a test order cancellation, a therapeutic (remedial or medicinal) drug monitoring, a creatinine clearance testing, a multi antibiotic therapy (analysis), a specific antibiotic therapy (analysis) and a blood ferritin serum test. Accordingly, in some embodiments, a computing server of an information system may be configured to select a testing task from the group consisting of at least one of a new test order, a new test order and a new sample order, a test order modification, a test order cancellation, a therapeutic (remedial or medicinal) drug monitoring, a creatinine clearance testing, a multi antibiotic therapy (analysis), a specific antibiotic therapy (analysis) and a blood ferritin serum test.

In some embodiments, an information system and/or the computing server of the information system may be configured to receive the instrument data set from the at least one external laboratory instrument and/or from a set of external laboratory instruments. Accordingly, in some embodiments, a computing server may be configured to receive a plurality of instrument data subsets from a plurality of external laboratory instruments, and the computing server may be configured to generate the instrument data set based on the plurality of instrument data subsets. Such a computing server may be configured to store the instrument data set in a data storage of the information system. Further, in some embodiments, the information system and/or the computing server may be configured to receive the history data set from the at least one external patient data information system and/or from a set of external patient data information systems. Accordingly, in some embodiments, the computing server may be configured to receive a plurality of history data subsets from a plurality of external patient data information systems, and the computing server may be configured to generate the history data set based on the plurality of history data subsets. The computing server may be configured to store the history data set in a data storage of the information system. Further, in some embodiments, the computing server may be configured to generate the test management data set, e.g. by merging, linking and/or combining the history data set and the instrument data set. The computer server may further be configured to apply the test management rules to the generated test management data set in order to generate the testing task. The computing server may further be configured to update a set of test orders maintained by the at least one external patient data information system based on the generated testing task. In other words, the computing server may be configured to provide update information and/or update data relating to and/or associated with the generated testing task to the at least one external patient data information system. The update information may refer e.g. to a modification of a test order, a cancellation of a test order, a request for a new test order and/or a request for a new sample order. Accordingly, the test management data set may refer to a comprehensive data set including any available information of a patient and/or any data relating to sample testing of this patient. This test management data set may then be comprehensively evaluated by applying the test management rules and a corresponding update information for the set of test orders may be generated and/or provided to the at least one external patient data information system based on the generated testing task.

As set forth herein, in some embodiments, by means of an information system for managing medical testing new associations between samples and diagnoses may be recognized. This may particularly be due to the comprehensive test management data set and the application of the test management rules to the test management data set, which may allow to comprehensively analyze any data available for a certain patient. In turn, this may lead to a reduced turn-around time from collection of an initial sample to completion of a final test and diagnosis for a particular patient. Moreover, due to the sensitivity and unstable nature of many bodily fluids and tissue samples, this reduced turn-around time may improve accuracy and precision of test results, potentially leading to improved diagnosis and patient outcomes as well as reduced inefficiencies in testing.

According to a first embodiment of a first aspect, the information system may further comprise a display interface, wherein the display interface is configured to provide data that, when rendered by a receiving device, displays a graphical user interface, wherein the graphical user interface comprises a description of an update of the set of test orders. This may allow a user of the graphical user interface to visually analyze the update of the set of test orders.

According to a second embodiment of the first aspect or of the first embodiment, the rules engine of the computing server may be further configured to apply the set of test management rules to the test management data set in response to a change in the test management data set. Therein, the change in the test management data set is associated with one or more of a new test result in the instrument data set received from the at least one external laboratory instrument, a new patient diagnosis in the history data set received from the at least one external patient data information system, a change in the set of test orders, and a change in the set of test management rules. In other words, the computing server of the information system may be configured to dynamically modify and/or update the test management data set. Further, the computing server may be configured to determine a change and/or a modification in the test management data set and to apply, using the rules engine, the test management rules to the test management data set in response to the determined change. By way of example, the test management data set may be updated continuously and/or after a certain time interval and the computing server may check for any change in the history data set, the instrument data set and/or the test management data set. This may enable the information system to comprehensively and quickly react to any change in the test management data set.

According to a third embodiment of the first aspect or of any of the first embodiment or the second embodiment, a rules engine may be configured to generate the testing task based upon a new test result in the test management data set, wherein the change in the set of test orders is selected from the group consisting of a new test order and a repeat test order. In other words, the computing server may be configured to determine a change in the test management data set associated with a change in the set of test orders, which change in the set of test orders is at least one of a new test order and a repeat test order. Further, the computing server and/or the rules engine may be configured to generate the testing task in response to determining the change in the test management data set and/or the change in the set of test orders.

According to a fourth embodiment of the first aspect or of any of the first, second, and third embodiments, a rules engine may be configured to generate the testing task based upon a new piece of data in the test management data set, wherein the testing task is selected from the group consisting of a new test order and a new sample and test order. In other words, the computing server may be configured to determine the new piece of data in the test management data set and the rules engine of the computing server may be configured to generate a new test order and/or a new sample and test order in response thereto. The new piece of data may for instance refer to a new sample test order being entered by a clinician at the at least one external laboratory instrument and/or the at least one external patient data information system. Also, the new piece of data may refer to e.g. a patient medical record being created or updated, a test result being generated at the at least one external laboratory instrument, a software update and/or an update of the test management rules.

According to a fifth embodiment of the first aspect or of any of the first to fourth embodiments, the rules engine may be configured to generate the testing task based upon a new piece of data in the test management data set or a change in the set of test orders, wherein the testing task is selected from the group consisting of a test order modification and a test order cancellation. In other words, the computing server may be configured to determine the new piece of data in the test management data set and the rules engine may be configured to modify a test order and/or to cancel a test order.

According to a sixth embodiment of the first aspect or of any of the first to fifth embodiments, the rules engine may be configured to generate the testing task based upon at least one of a patient age, a patient identity, and a present medical condition of a patient, wherein the testing task is therapeutic (remedial or medicinal) drug monitoring.

According to a seventh embodiment of the first aspect or of any of the first to sixth embodiments, the rules engine may be configured to generate the testing task based upon at least one of a serum creatinine level and a past medical condition of the patient, wherein the testing task is creatinine clearance testing.

According to an eighth embodiment of the first aspect or of any of the first to seventh embodiments, the rules engine may be configured to generate the testing task based upon one or more of microbiologic test results and blood culture test results, wherein the testing task is one or more of multi antibiotic therapy (analysis) and specific antibiotic therapy (analysis).

According to a ninth embodiment of the first aspect or of any of the first to eighth embodiments, the rules engine may be configured to generate the testing task based upon one or more of a) a medical diagnosis of the patient, b) a previous test result of the patient comprising one or more of B12, EPO, or Ferritin, c) a demographic information of a patient, and d) blood coagulation status, wherein the testing task is a blood ferritin serum test.

According to a tenth embodiment of the first aspect or any of the first through ninth embodiments, the rules engine may be configured to generate the testing task based upon one or more of the patient's temperature, the patient's pulse, the patient's blood oxygenation, or a previous test result of the patient comprising one or more of PCT, IL-6, CRP or ESR, wherein the testing task is detecting sepsis or monitoring sepsis.

According to an eleventh embodiment of the first aspect or any of the first through tenth embodiments, the rules engine may be configured to generate the testing task from a group consisting of remedial drug monitoring, creatinine clearance testing, multi-antibiotic analysis, specific antibiotic analysis or blood ferritin serum analysis.

According to a tenth embodiment of the first aspect or of any of the first to ninth embodiments, the information system may further comprise an analytics component, wherein the analytics component is configured to receive a set of performance data from the computing server. Therein, the set of performance data comprises information describing an input and an output of the rules engine, and wherein the analytics component is further configured to provide a modification to the rules engine based upon the set of performance data. The performance data may refer to e.g. data indicating a performance of the information system, the at least one laboratory instrument and/or the at least one patient data information system. Among others, the performance data may be used to create and/or revise the set of test management rules and/or identify laboratory instruments that may need to be updated, e.g. by replacing reagents in the respective laboratory instrument. Generally, this may allow to change and/or update the information system over time based on the performance data in order to reflect new developments in patient care and/or sample testing.

According to an eleventh embodiment of the first aspect or of any of the first to tenth embodiments, the computing server may be selected from the group consisting of a cloud based computing environment, a dedicated server, and a software process on a multi-function server. Accordingly, in some embodiments an information system may be implemented in various ways according to specific needs.

According to a second aspect, a cross-discipline system for managing medical testing may be provided. The cross-discipline system may comprise an information system, as described above and in the following with reference to the first aspect of the invention and/or with reference to any of the first to eleventh embodiments of the first aspect. The cross-discipline system may further comprise at least one laboratory instrument, and at least one patient data information system configured to maintain a patient data set comprising a set of test orders and a history data set. Therein, the at least one laboratory instrument may be communicatively coupled to the computing server of the information system via the instrument communication interface of the information system, wherein the at least one patient data information system may be communicatively coupled to the computing server of the information system via the information system interface of the information system.

It should be noted that features, functions, characteristics, elements, functionalities and/or functional modules of the information system, as described above and in the following with reference to the first aspect of the invention and/or with reference to any of the first to eleventh embodiments of the first aspect, may be features, functions, characteristics, elements, functionalities and/or functional modules of the cross-discipline system, as described above and in the following. Vice versa, features, functions, characteristics, elements, functionalities and/or functional modules of the cross-discipline system, as described above and in the following, may be features, functions, characteristics, elements, functionalities and/or functional modules of the information system as described above and in the following with reference to the first aspect of the invention and/or with reference to any of the first to eleventh embodiments of the first aspect.

According to a third aspect, a method for operating an information system for managing medical testing may be provided, wherein the information system comprises a computing server, an instrument communication interface communicatively coupled with at least one external laboratory instrument, and an information system interface communicatively coupled with at least one external patient data information system, which external patient data information system is configured to maintain a patient data set comprising a set of test orders and a history data set. Such a method may comprise steps of:
  a) receiving, with the computing server and/or with a first receiving section of the computing server, an instrument data set from the at least one external laboratory instrument via the instrument communication interface,
  b) receiving, with the computing server and/or with a second receiving section of the computing server, a history data set from the at least one external patient data information system via the information system interface,
  c) building and/or generating, with the computing server and/or with a test management section of the computing server, a test management data set based on the received instrument data set and based on the received history data set, d) generating, with the computing server and/or with a rules engine of the computing server, a testing task based on applying a set of test management rules to the test management data set, and e) updating, with the computing server and/or with an updating section of the computing server, a set of test orders of a patient data set maintained by the at least one external patient data information system based on the generated testing task. Therein, the term "updating" may refer to providing update information to the at least one external patient data information system.

Therein, the instrument data set comprises test results associated with a patient, and the history data set comprises at least one of biographical and historical information associated with the patient.

In some embodiments of the third aspect, the testing task may be performing a test on the sample, wherein the test to be performed on the sample is detecting sepsis or monitoring sepsis. Similarly, in some other embodiments of the third aspect, the testing task may be performing a test on the sample wherein the test to be performed on the sample is a test for one or more inflammation marker, said inflammation marker being selected from the group consisting of ESR, CRP, IL-6 and PCT.

It should be noted that features, functions, characteristics, elements, functionalities and/or functional modules of the information system, as described above and in the following with reference to the first aspect of the invention and/or with reference to any of the first to eleventh embodiments of the first aspect, may be features, functions, characteristics, elements, functionalities, functional modules and/or steps of the method according to the third aspect, as described above and in the following. Vice versa, features, functions, characteristics, elements, functionalities, functional modules and/or steps of the method, as described above and in the following with reference to the third aspect, may be features, functions, characteristics, elements, functionalities and/or functional modules of the information system as described above and in the following with reference to the first aspect of the invention and/or with reference to any of the first to eleventh embodiments of the first aspect. Similarly, features, functions, characteristics, elements, functionalities and/or functional modules of the cross-discipline system according to the second aspect of the invention, as described above and in the following, may be features, functions, characteristics, elements, functionalities, functional modules and/or steps of the method, as described above and in the following, and vice versa. In other words, any features, functions, characteristics, elements, functionalities, functional modules and/ or steps as described above and in the following with reference to any of the first, second and third aspects may be features, functions, characteristics, elements, functionalities, functional modules and/or steps of any other aspect of the invention, as described above and in the following.

According to a fourth aspect, a computer program element may be provided, which when executed on a computing server of an information system for managing medical testing according to the first aspect of the invention and/or according to any of the first to eleventh embodiments of the first aspect, instructs the computing server to carry out the steps of the method according to the third aspect.

According to a fifth aspect, a computer-readable medium may be provided, on which a computer program element according to the fourth aspect is stored.

These and other aspects of the invention will be apparent from and elucidated with reference to the exemplary embodiments described hereinafter with reference to the attached drawings.

The technology disclosed herein may be implemented in order to improve the efficiency of sample testing. An information system for managing medical testing and/or a cross-discipline system for managing medical testing, such as e.g., a software driven cross discipline test result interpretation and patient result management system, may use a set of test management rules to automate the creation of tasks for rerunning, reflexing, retesting, or otherwise performing additional collection and testing of new or old samples, and may also automate the cancelation or modification of existing tasks when necessary. The test management rules, a rules engine and/or a computing server of an information system for managing medical testing may receive a variety of input data in order to decide when creation or modification of testing orders should occur. Input data could include, for example, sample quality indicators (e.g. lipemic, hemolytic, short sample, plasma versus serum, and others), sample age, creation or modification of an associated test order (e.g. a cross-discipline test being ordered from another piece of equipment for that sample or that patient), patient history and demographic factors, manual or automated flagging or validation, new patient diagnosis, and other data. Using the test management rules, a rules engine and/or a computing server of an information system for managing medical testing may receive and process such data, new associations between samples and diagnoses may be recognized leading to an improved turn-around time from collection of an initial sample to completion of a final test and diagnosis for a particular patient. Due to the sensitivity and unstable nature of many human body fluid and tissue samples, this improved speed may improve accuracy and precision of results, leading to better diagnoses and improved patient outcomes as well as reduced inefficiencies in testing.

In some embodiments, samples, which may be a number of different fluids, may be collected from a patient for performing tests one or more laboratory instruments. In some embodiments, request may be received for at least one test to be performed on a sample by a clinician and/or a lab technician, wherein the test is associated with a set of pre-defined parameters, which parameters may be technical parameters set by the clinician. In some embodiments, based on the selected test, an intermediate layer situated between the laboratory instrument which would perform the tests and an external system (e.g., an LIS or HIS), such as middleware, could route the sample to a plurality of laboratory instruments that are configured to perform the test and report the results to the intermediate layer/middleware. In some embodiments, such an intermediate layer/middleware may be interfaced with a LIS, and the intermediate layer/middleware may maintain information indicating laboratory instruments it is interfaced with and what tests those instruments can perform. In some other embodiments, results obtained from a plurality of lab instruments may be compared by the middleware to determine if they are outside a specified range for a plurality of parameters. Such parameters may have a threshold limit set, and such limit may be based on the particular underlying laboratory instruments and/or on analysis of historical data. In some embodiments, a specified range for use in analyzing test results may be comprised by a set of pre-defined parameters in the intermediate layer/ middleware. In some embodiments, an intermediate layer/ middleware may be configured to report the results of a test to a laboratory information system or other external system (e.g., a HIS). Further, in some embodiments, if a test result is determined to be outside of a specified range (e.g., either less than or greater than the range's minimum or maximum values) then an intermediate result/middleware may be configured to predict that the patient corresponding to that result may be subject to an infection/disease. Alternatively (or additionally), in some embodiments, when a result is outside a specified range, middleware may be configured to route the sample to a lab instrument different from the instrument that performed the original test, and to cause such instrument to perform a reflex test on the sample. In some embodiments, a laboratory instrument may be configured to report the result of a reflex test to the middleware, and values outside of a predefined range (either of the original test or a reflex test or both) may be flagged. In some embodiments, results may be sent from the middleware to a laboratory information system after reflex testing has taken place.

I. Cross Discipline Test Result Management System

Turning now to the figures, FIG. 1 shows a schematic diagram of an exemplary information system 100 for managing medical testing and/or an exemplary cross-discipline system 500 for managing medical testing. The exemplary information system 100 and/or the exemplary cross-discipline system 500 may be configured to manage and react to test results from one or more test instruments, which may be located within a single lab, in different labs within a single organization (e.g., different labs in a single hospital), or even different locations all together (e.g., at multiple outside laboratories). In FIG. 1, a middleware hub 100 is connected to one or more laboratory instruments 106 108 110 through an instrument communication interface 101 and is configured to receive test results from those instruments. Therein, the middleware hub 100 may refer to the information system 100 for managing medical testing. One or more computing servers 107 of the middleware hub 100 are configured to aid in processing and handling test results and other data using a rules engine and other processing rules. The at least one computing server 107 comprises a first receiving section 107a, a second receiving section 107b, a test management section 107c, a rules engine 107d, and an updating section 107e. By way of non-limiting example, middleware hub 100 can reside in a cloud computing environment and may comprise one or more servers in one or more data networks. The server may be a collection of servers. In one non-limiting example, a database on one or more of the servers may be a collection of databases. Alternatively, the middleware hub 100 may be a standalone device such as a server that is connected directly to, or connected to the same network as the test instruments 106 108 110, or may be software running on a separate device such as a laboratory information system ("LIS") 102, wherein the laboratory information system 102 may refer to a patient data information system 102. When implemented as a standalone device, a middleware hub 100 may be in communication with other servers, such as analytics server 104 (which may be implemented as one or more servers), or may perform the tasks of the analytics server 104 or computing server 107 using available resources. In many conventional laboratory systems, the laboratory instruments 106 108 110 may be connected directly to the LIS 102 over a network, with data generated by the instruments going directly to the LIS 102. In some implementations of the disclosed technology, the middleware hub 100 may be inserted into this data flow on the communication path between the instruments 106 108 110 and the LIS 102 (or, such as in embodiments where laboratory instruments are located at different outside laboratories, the middleware hub 100 may be located on the communication paths between each of the laboratory instruments and its respective LIS), with an information system interface 105 allowing communications between the LIS 102 and the middleware hub 100. In some implementations, the middleware hub 100 may provide additional instructions to the laboratory instruments 106 108 110 in order to create, cancel, or modify test orders for the instruments 106 108 110 to execute.

Based on its placement in the communication path between the LIS 102 and the laboratory instruments 106 108 110, the middleware hub 100 may also be configured to process test results from the laboratory instruments 106 108 110 before providing them to the LIS 102. Depending upon a particular implementation, the middleware hub 100 may provide all test result data to the LIS 102 in near real-time without modification, or may prioritize the flow of data to the LIS 102 in order to improve on the efficiency of test result reporting. For example, if the middleware hub 100, upon receiving a first test result for a first patient, determines that a second test result for that patient is also currently being generated by one of the laboratory instruments, the middleware hub 100 may throttle delivery of those associated results so that they arrive at the LIS 102 at substantially the same time. This may allow a technician viewing results at the LIS 102 to view the results together in a context that might allow for better diagnosis. This is especially true where a technician might be examining results on the LIS 102 from a multitude of patients as the results arrive, even where they provide an incomplete picture. The middleware hub 100 may also be configured to provide instructions to the LIS 102 causing test orders to be created, canceled, or modified.

In some implementations, the middleware hub 100 may also have or be connected to an analytics server 104 and be configured to provide data indicating the performance of the system so that this data can be used to create or revise test management rule sets, identify laboratory instruments that may need to be updated (e.g., by replacing reagents currently used by those instruments in testing), or make other changes to the system. For example, analytics server 104 may be used to provide a software update to one or more middleware hubs 100 that may include additional or revised rules or logic for processing and handling data. This may allow the operation of the middleware hub 100 to be changed over time in order to reflect new developments in patient care or sample testing. This could also allow important information on testing instruments or testing supplies to be disseminated and acted upon. For example, if it is determined that a particular set of testing instruments, or a particular batch of reagents is defective, the analytics server 104 could provide such data or revised software processes to the middleware hub 100 that could be used to retest affected samples or otherwise avoid relying upon possibly erroneous test results or equipment.

The middleware hub 100 may also be connected to a hospital information system ("HIS") 103 via the information system interface 105. The hospital information system 103 may refer to a patient data information system 103. The middleware hub 100 may receive or access information from the HIS 103 such as patient medical history, allergies, prescriptions, patient demographic data, employee data such as available lab technicians, facility data such as types testing laboratories and testing instruments that may be available at various testing laboratories, and other similar data. Such data may be used to, for example, identify additional testing procedures or diagnoses based upon patient history and demographics, or more efficiently create, assign, and modify testing orders across multiple testing instruments and multiple technicians. Other systems and devices may be added to those shown in FIG. 1 and will be apparent to one of ordinary skill in the art in light of this disclosure. These devices may include, for example, backup or storage drives, display devices, communication devices, and sound devices for creating notifications, alarms, or other interactions with technicians, clinicians, and other personnel, backup power supplies, backup network and communication devices and channels, and other devices.

The middleware hub 100 may also be connected to one or more graphical user interfaces 111 via a display interface 109. The graphical user interface 111 may be used by a user to manage configurations of the middleware hub 100, view test results or other information handled by the middleware hub 100, or view other information and results.

In the following the main functionality provided by the middleware hub 100 and/or the information system 100 in some embodiments for managing medical testing is briefly summarized. The middleware hub 100 and/or the information system 100 for managing medical testing may be configured to receive by means of the first receiving section 107a of the computing server 107 an instrument data set from at least one of the laboratory instruments 106, 108, 110 via the instrument communication interface 101. Further, the middleware hub 100 and/or the information system 100 may be configured to receive by means of the second receiving section 107b of the computing server 107 a history data set from at least one of the patient data information systems 102, 103 via the information system interface 105. Moreover, the test management section 107c of the computing server 107 may be configured to generate a test management data set based on the instrument data set and the history data set. Further, the rules engine 107d of the computing server 107 may be configured to apply a set of test management rules to the test management data set in order to generate a testing task. Further, the updating section 107e of the computing server 107 may be configured to update a set of test orders of a patient data set maintained by at least one of the patient data information systems 102, 103.

In some embodiments, the laboratory instruments 106, 108, 110 may provide technical validation, flagging information for interpreting specific test results. This information may be in addition to or as an alternative to service parameters for technical performance monitoring, reagent lot numbers, and open stability as well as individually performed quality control results for different test levels. In some embodiments, such information may be stored at the laboratory instruments 106, 108, 110 and may not be transferred to the LIS 102. In some embodiments, an enhanced middleware solution may maintain this type of data, along with data on patient demographics, sample material and conditions, and/or previous results across disciplines. This may allow for result interpretation beyond the capabilities of the LIS 102. In some embodiments, this may be supported because a middleware solution (e.g., middleware hub 100) may use an intelligent dynamic communication protocol for interactions with laboratory instruments 106, 108, 110, as opposed to a more limited communication protocol which may be used by the LIS 102.

In some embodiments, a HIS 103 may send a test request to a LIS 102, potentially along with the patient's demographic data, disease statement, and other information. The LIS 102 may send the relevant data with the test request to middleware. In some embodiments, the middleware may have information from each of the laboratory instruments 106, 108, 110. This information may include which tests are available on each analyzer, which tests are calibrated on each laboratory instrument (analyzer), the status of each reagent on each analyzer, etc. In some embodiments where this information is present, a middleware hub may use it to create a work list for each analyzer/laboratory instrument and may then send it to the appropriate analyzers. In the case of a fully automated analyzer, this may then be implemented via a track on the analyzer, or, if in a standalone environment, a manual worklist may be provided for the analyzer's operator. In embodiments where lab instruments are located in multiple rooms, middleware can provide a virtual bridge between instruments, and can initiate cross discipline reflex testing. In other embodiments, this may be implemented using a hub and spoke network layout. In some embodiments, middleware may communicate directly with analyzers and send specific test requests to the analyzers which would perform the appropriate tests. The analyzer(s) may then send the test results back to the middleware. In some embodiments, if a result is outside of a defined reference range, or if it has a specific flag, the middleware may initiate reference testing on another analyzer. Such reflex testing may be on another analyzer on the same track with the analyzer that provided the original test, or may be on another analyzer at a separate location. The results of this reflex testing may be sent back to the middleware by the analyzer which performs the testing, and that result may, in turn, be sent from the middleware to the LIS and/or HIS.

II. Methods of Cross Discipline Test Result Management

FIGS. 2-6 show steps and methods that may be performed by a configured device, such as the middleware hub 100, the information system 100 for managing medical testing, the cross-discipline system 500 for managing medical testing, a computing server 107 and/or any other device configured to operate as a middleware hub 100, in order to manage and react to new data becoming available such as test results as they are generated by one or more laboratory instruments 106 108 110, patient data from a HIS 103, order data from an LIS 102, and/or software configuration changes from an analytics server 104.

Figure 2:
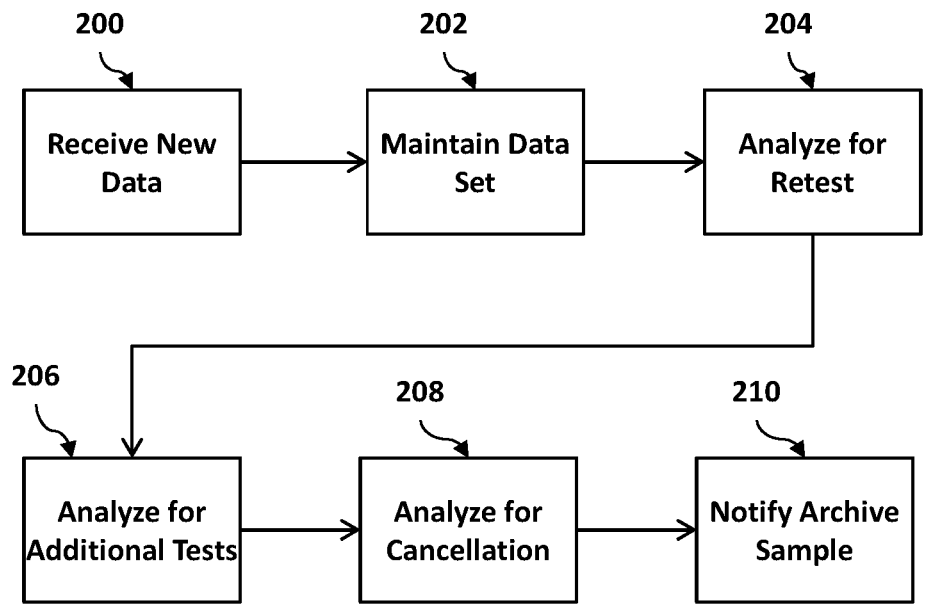
FIG. 2 is a flowchart of an exemplary set of high-level steps that a system could perform to manage and react to output of test instruments with a middleware hub.

FIG. 2 shows one exemplary set of steps that may be performed by a device such as the middleware hub 100, the information system 100 for managing medical testing, and/or the cross-discipline system 500 for managing medical testing in order to react to and analyze new data as it becomes available. Though some of the steps shown in FIGS. 2-6 may be discussed as occurring immediately after the arrival of new test results or other data, it should be understood that many of the steps may be performed in an ongoing manner since the data set that may impact whether new tests are needed or currently scheduled tests should be canceled may be constantly changing. While actual system performance may vary greatly depending upon factors such as the number of patients and laboratory instruments that a particular middleware hub 100 serves as well as the speed at which the middleware hub 100 can access and manipulate data, it should be understood that in at least some cases the middleware hub 100 may react to some high priority occurrences, such as the arrival of new test data, while other lower priority tasks, such as reviewing existing lab orders for cancellation, may be performed only as processing cycles are available. Accordingly, it should be understood that the disclosed system may be variously configured to be reactive to the arrival or availability of new data to the middleware hub 100, in addition to or in the alternative to handling certain types of new data at different times based upon the priority of such data or the availability of processing time.

During operation one or more of the devices or components of the middleware hub 100 (e.g. the LIS 102, HIS 103, a test instrument 106, 108, 110, and/or analytics server 104) may produce new data that may be provided to or accessed by the middleware hub 100. New data could include, for example, a new sample test order being manually entered by a clinician at the LIS 102, a patient medical record being created or updated at the HIS 103, a test result being generated at a lab instrument 106, 108, 110, or a software update, test management rule set update, or data set refresh instruction from an analytics server 104.

As this data is generated and becomes available in the LIS 102, HIS 103, or other hospital systems, this data as well as other data may be provided to or accessed by the middleware hub 100 and maintained 202 with respect to test results or patients that it may be associated with. Such maintenance could include copying data into a new storage location or creating associations between data in existing locations so that it may be more readily accessed at a later time. A test management data set for a new patient may be somewhat sparse and may only contain information on the patient's history, demographics, and current medical event. However, for other patients, the test management data set may include sample test results for a variety of past and present procedures, information on testing instruments used to perform those procedures, sample collection and storage information relating to those procedures, and other information.

As the test management data set is maintained and evolves over time as more information becomes available, the test management data set may be provided as input to a rules engine that is configured to implement the test management rules and determine if a sample retest 204 is needed, whether additional new tests are needed 206, and whether presently ordered tests may be modified or canceled 208. After determining that no further testing is needed on a particular sample, based upon, for example, the test management data set and presently ordered tests associated with the sample, a notification may be generated by the middleware hub 100 at the LIS and/or in response to a corresponding signal provided by the middleware hub 100 to the LIS 102 or another system indicating that the sample may be archived 210. By way of example, the middleware hub 100 may be configured to provide a signal to the LIS 102 and/or the HIS 103, which signal may comprise message information, e.g. for a notification message to be output at the LIS 102 and/or the HIS 103.

Figure 3:
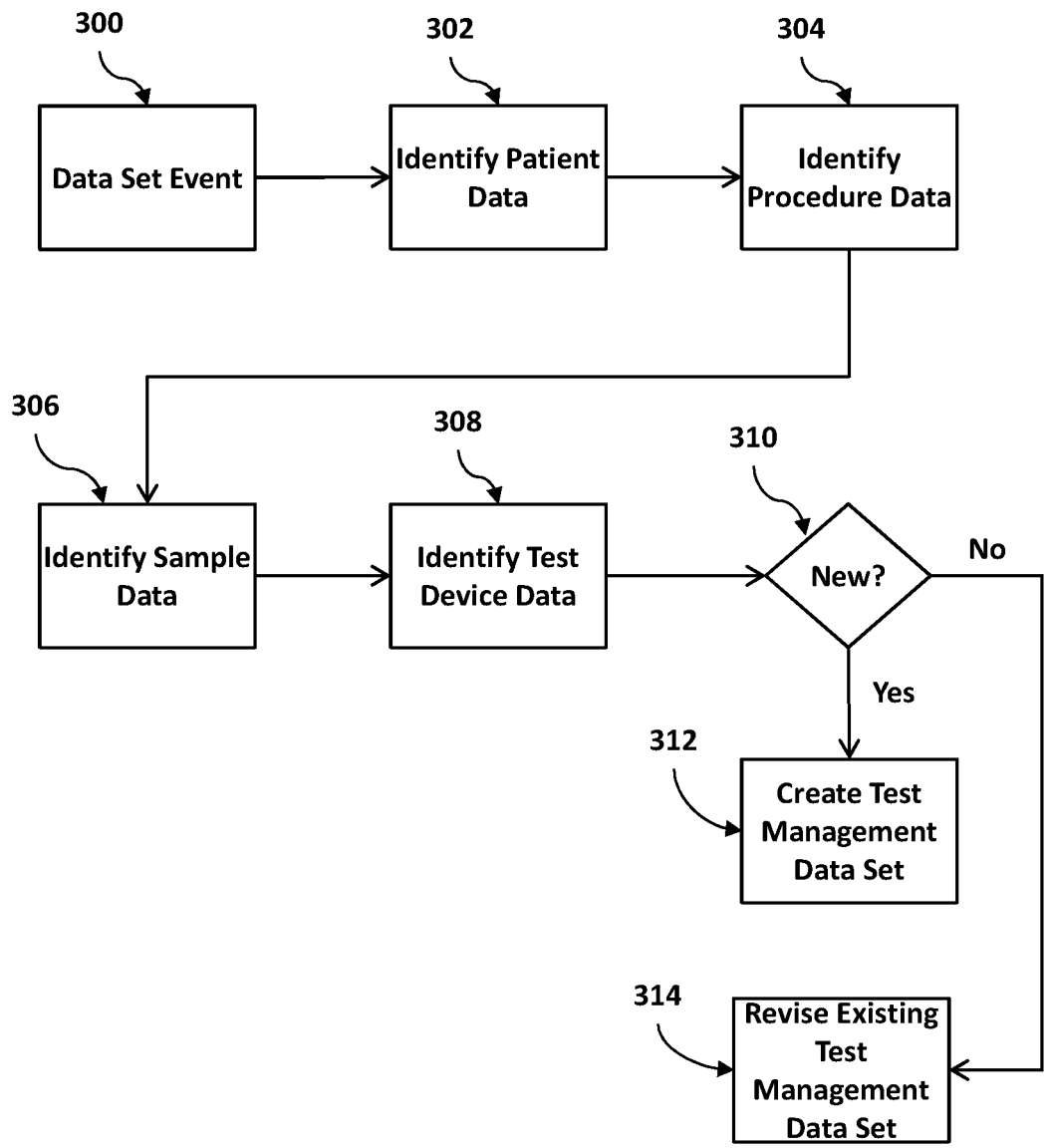
FIG. 3 is a flowchart of an exemplary set of steps that a system could perform to prepare data from a variety of sources in order to more accurately identify deficiencies in testing results.

While the particular data and steps that are used to build a test management data set may vary by implementation, FIG. 3 shows one exemplary set of steps that the middleware hub 100, the information system 100 for managing medical testing and/or the cross-discipline system 500 for managing medical testing could perform to build and maintain a test management data set. While the steps of FIG. 3 are shown in one sequence for the sake of discussion, it should be understood that these steps could occur in many different sequences or in parallel as data becomes available. So, for example, the test management data set may be modified in near real-time as new data becomes available, or may be modified once per hour based upon a schedule, or may be flagged for revision and revised when processing time or database time becomes available, any of which may be referred to as a data set event. For example, as laboratory instruments produce data the middleware hub 100 may receive output from test instruments 106 108 110 indicating the results of a patient sample test. The availability of such new data may be recognized by the middleware hub 100 as the occurrence 300 of a data set event. Result data, or a subset of the result data may be retained or noted by the middleware hub 100 for later access, and then the result data may be passed along to the LIS 102 for normal storage. Result data that is retained or noted by the middleware hub 100 may include, for example, identification of a sample, the type of test performed on the sample, the numerical results of the test, any custom notes entered by a technician during the test, identification of a testing instrument, lot identifiers of reagents or supplies used during a test and other similar information that may be output by a testing instrument 106 108 110. Other data set events that may occur 300 could include, for example, new patient data being available from a HIS 103, new orders being available from an LIS 102, an indication from an analytics server 104 that a batch of reagents has been flagged as defective, the occurrence of a scheduled data set refresh time for data sets associated with one or more patients or more on or more samples, or the availability of data processing capabilities to access and process data previously received for one or more patients or one or more samples.

When data set events occur 300, the middleware hub 100 may identify and retain 302 a copy of or reference to patient data available on a patient that is associated with the data set event. Patient data could include physical characteristics of a patient such as height, weight, and gender, past medical histories such as previous diagnoses and procedures, and other information describing the patient that may be available in the HIS 103 or another hospital system and which may be helpful in diagnosing a medical condition (e.g., identification of a propensity for developing a disease) or determining testing needs. The middleware hub 100 may also identify and retain 304 a copy of or reference to procedure data available for the current procedure a patient is undergoing. This could include such information stored on the HIS 103 or another hospital system such as the patient's present location, reason for admission, chronology of samples gathered from the patient, procedures performed on the patient, and other similar information that indicates what has occurred with the patient since admission.

The middleware hub 100 may also identify and retain 306 a copy of or reference to sample data available for the patient. This could include identification of each sample gathered, type of sample, time of collection for each sample, current location of each sample, and other information which may indicate what has occurred since sample collection and whether the sample is still viable. Such data may be available on the LIS 102, HIS 103, or another hospital system. The middleware hub 100 may also identify and retain 308 a copy of or reference to test instrument data that is associated with samples for a patient. This could include identification of test instruments, location of test instruments, personnel that have accessed test instruments, model, serial number and manufacturer of test instruments, software or firmware versions for test instruments, maintenance dates and calibration records or settings for test instruments, lot numbers and recall status of reagents, test instruments, or other testing supplies used during a test, and other information which may indicate the accuracy or precision of results from a particular test instrument. Such data may be available in the results provided by the instruments 106 108 110 themselves, and/or on the LIS 102, HIS 103, the analytics server 104, or another hospital system.

As this data becomes available to the middleware hub 100, the middleware hub 100 may determine if a test management data set already exists 310 for the patient or sample associated with the newly available data or data set event. The test management data set may be uniquely identified in various ways depending upon the capabilities of a particular system, for example, each unique patient may have a test management data set containing data associated with that patient, with sample related data being a sub-object of the unique patient. Alternatively, the test management data set may be organized such that each unique sample has a test management data set containing data associated with that sample, with patient data being a sub-object of that unique sample. If it is determined 310 that a particular test management data set already exists, the existing data set may be revised and/or updated 314 based upon the newly available data. If it is determined 310 that a new test management data set should be created, it may be created 312 based upon the newly available data.

Figure 4:
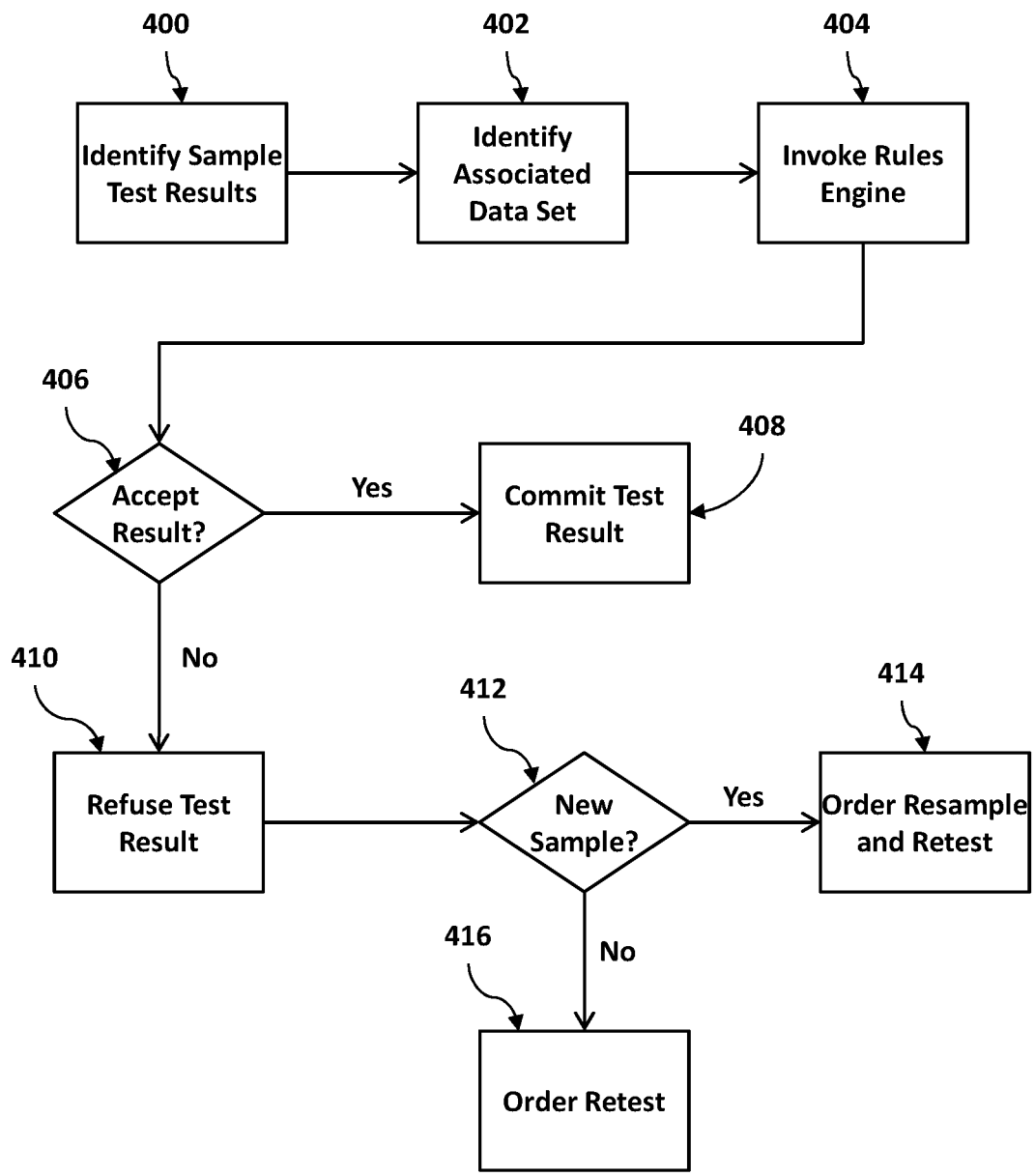
FIG. 4 is a flowchart of an exemplary set of steps that a system could perform using a set of rules to identify and address the need for a sample retest.

FIG. 4 shows one exemplary set of steps that may be performed by the middleware hub 100, the information system 100 for managing medical testing, and/or the cross-discipline system 500 for managing medical testing to rapidly provide an indication that a sample should be retested or newly collected. When new data becomes available, such as a new test result, the sample may be identified 400 by the system, which may also identify 402 a test management data set associated with that sample or a patient associated with that sample. With a sample result and an updated test management data set that reflects the newly available information, a rules engine configured to apply the test management rules may be invoked 404 in order to determine, based upon the sample result and the test management data set associated with the sample result, whether the sample result is likely to be precise and accurate.

The test management rules may be, for example, a set of Boolean rules that examines the test management data set for specific occurrences, such as improper age or storage of a sample, or a specific characteristic or result from an associated sample test. While in some cases a single characteristic or occurrence evaluating as true might indicate that the test result was not acceptable, such as where test instrument information indicates a critical software error likely contributed to an inaccurate result, in other cases a number of evaluations of true or false for two or more occurrences may be required in order to mark a test result as unacceptable. For example, in one case it may be that the rules engine must determine both that the tested sample was too old when tested, and that the test sample had not been stored or preserved in between collection and testing, in order to make a determination that the test result is not acceptable.

If the rules engine determines that the results of the test are acceptable 406, the test result may be committed 408 which may include one or more of flagging the result as acceptable, passing the result to the LIS 102, passing the result to an analytics server 104, or other actions when the test result is newly available, or flagging a prior test result as having been checked and verified when it has been checked based upon other newly available data. If the result is determined to be unacceptable 406, the result may be refused 410, which may include flagging the result as unacceptable in some way and passing the result to one or more of the LIS 102, the analytics server 104, or another system. After refusing 410 a test result, it may be determined whether previously collected sample is still usable for retesting 412 based upon the type of sample, the age of the sample, storage procedures for the sample, and the availability of the patient for collection of a new sample. Where it is determined that a new sample is not needed or that it is otherwise unavailable, a retest of the previous sample may be automatically ordered 416 by the middleware hub 100. Retest could include, for example, the repeat performance of a previous on the same sample, but could also include reinterpreting the data or results generated from a previous test in light of newly available information. For example, if data from the LIS 102 or analytics server 104 indicates that a particular test instrument 106 is measuring certain characteristics consistently high, the test results may be reprocessed and newly generated to adjust for this known inaccuracy. Where it is determined that a new sample is needed, a new sample and retest may be automatically ordered 414 by the middleware hub 100. The middleware hub 100 may order new collection and new testing by creating records on or communicating directly with the LIS 100, directly with one or more of the test instruments 106 108 110, or directly with one or more personnel via mobile devices or other communication channels.

Figure 5:
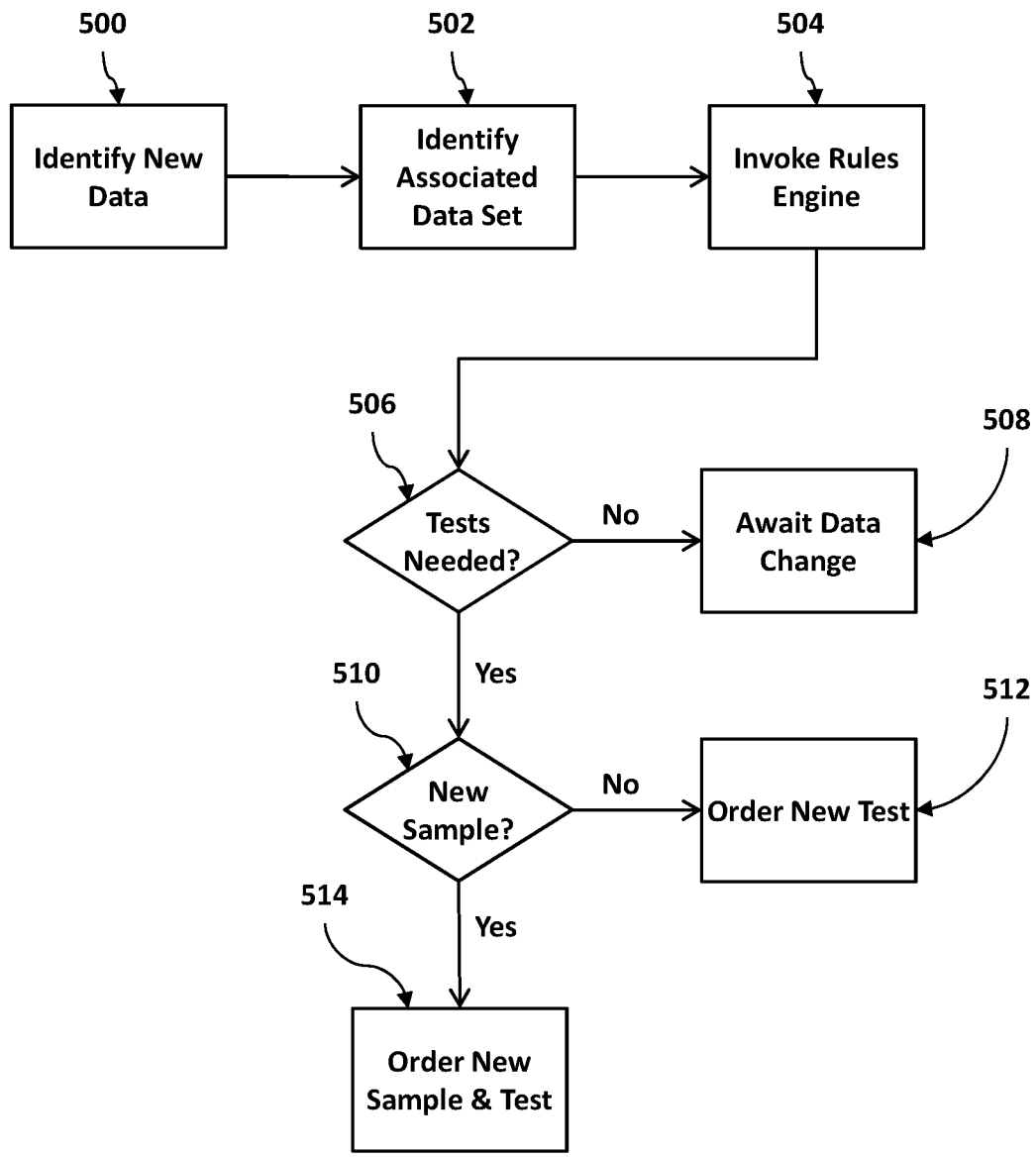
FIG. 5 is a flowchart of an exemplary set of steps that a system could perform using a set of rules to identify and address the need for additional testing.

FIG. 5 shows one exemplary set of steps that the middleware hub 100, the information system 100 for managing medical testing, and/or the cross-discipline system 500 for managing medical testing could perform to determine when additional testing is needed. Initially, the system may identify 500 newly available data that may impact the need for additional testing. This could include, for example, a new test result, a new piece of patient data such as a blood pressure reading or heart rate reading, a new medical event or medical procedure, or other similar data that may become available during the course of treatment. The system may then identify 502 the test management data set that is associated with that newly available data. For example, if the new data is a test result for another test, the system may identify 502 the patient that the new test result is for, and a test management data set that is unique to that patient. The rules engine may then be invoked 504 to determine, based upon the newly available data and associated test management data set, whether additional testing is needed 506.

This determination may be made based upon one or more test management rules being applied by the rules engine to the available data. For example, one rule may indicate the need for additional testing where the newly available data is a test result showing high white blood cell count, in the patient, and the test management data set indicates that the patient has a history of infections. If no additional testing is needed currently, the system may await 508 the introduction of additional data and take no other action currently. If additional testing is needed 506, the system may determine if that testing may be performed based upon currently available samples or whether additional samples must be collected from the patient. This determination may be made based upon available sample data such as the age and storage conditions of the sample. If no new sample is needed 510, additional testing may be ordered 512 using the available sample. If a new sample is needed 510, additional sample collection and testing may be ordered 514. As with previous examples, orders may be created by the middleware hub 100 by communicating with one or more of the LIS 102, the testing instruments themselves 106 108 110, or personnel mobile devices.

As an example, in one scenario a blood test result for a first characteristic may be received at the middleware hub 100 and identified 500 as new data that may impact or be impacted by other currently available data. The system may then identify 502 data from the test management data set that impacts or is impacted by the new data. This could include previous blood tests for the first characteristic, previous blood tests for other characteristics, testing of other samples or bodily fluids, patient medical history, patient demographic information, or other information associated with the patient or a test performed on a patient. The rules engine may then be invoked 504 using the identified 502 data set, including the newly available data, as inputs. In this manner, the newly available blood test for the first characteristic may be examined in the context of all previously available data to determine if additional testing of that sample or result is needed, or if additional testing of any type is needed.

For example, a blood test result showing the first characteristic may by itself not be of any major concern to a clinician or an automated process such as a patient monitoring device or tool. However, the rule engine may analyze this first characteristic and determine that, since the data set contains results from an earlier blood test for the first characteristic, the change in the first characteristic from the earlier test to the present test may be a cause for alarm or additional testing. The same could also occur in a manner that examines the test result for the first characteristic in the context of test results from one or more other samples, such as a urine sample, tissue sample, or other collected sample, or in the context of test results for other characteristics from the same sample, such as a second characteristic, a third characteristic, or both. A determination that additional testing is needed could include, for example, determining that the blood test should be re-rested for the first characteristic or newly tested for a second characteristic, or re-interpreting a previous test result in light of the newly available data on the first characteristic and determining that tests of another sample or characteristic should be newly performed or repeated.

Figure 6:
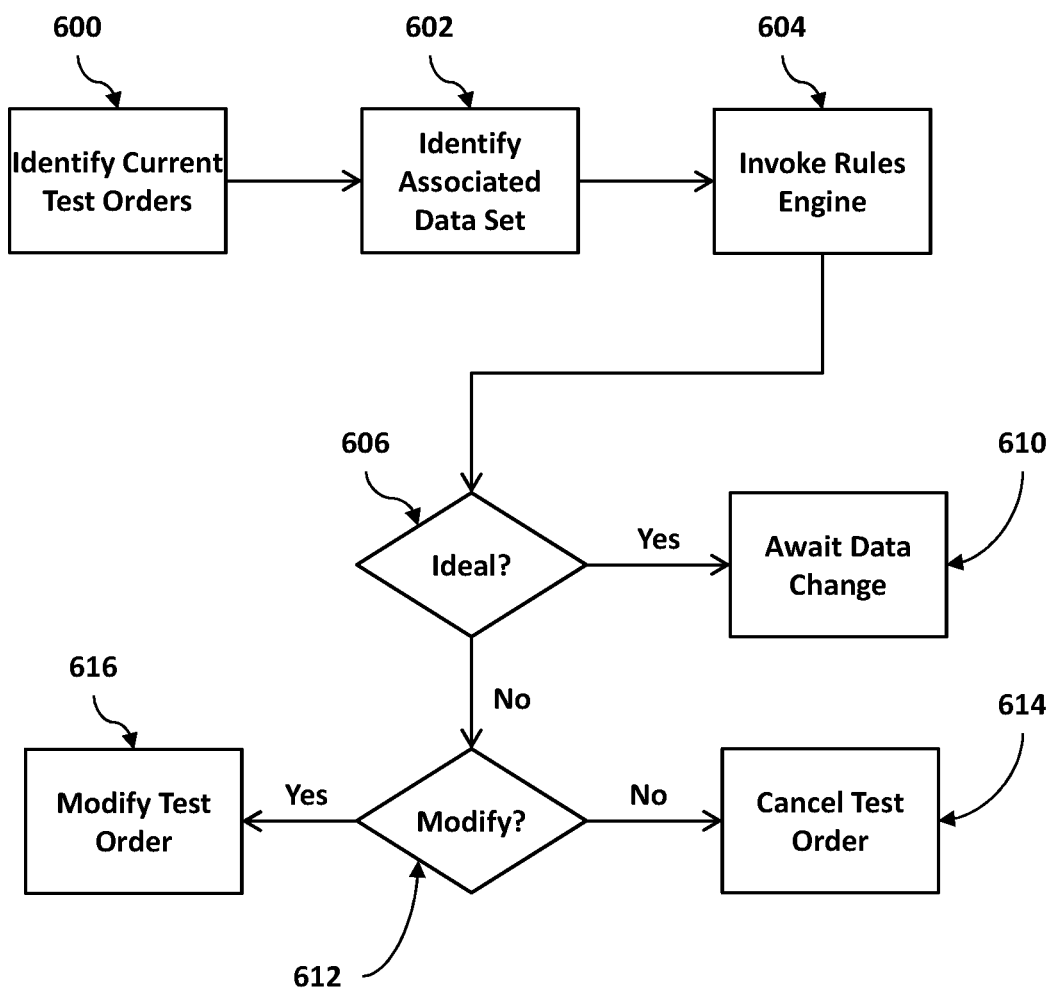
FIG. 6 is a flowchart of an exemplary set of steps that a system could perform using a set of rules to identify testing orders that may be canceled or modified.

FIG. 6 shows one exemplary set of steps that the middleware hub 100, the information system 100 for managing medical testing, and/or the cross-discipline system 500 for managing medical testing could perform to determine when currently ordered tests may be modified or canceled. Auditing of current test orders for modification or cancelation may occur, for example, when new data becomes available to the system, as directed by an analytics server 104 or other system, based upon a schedule, based upon available processing time, or other similar data set events. Initially, current test orders that relate to newly available data may be identified 600 by the system and a test management data set associated with those test orders may be identified 602. The rules engine may be invoked 604 to determine, based upon application of a set of test managements to the test management data set and the newly available data, whether the current test orders are ideal or not 606. For example, a test order for additional blood testing for white blood cell count may become irrelevant if the patient begins to present different symptoms after the test is ordered. In addition to avoiding the cost of performing the now irrelevant test, canceling the test may improve efficiency of testing overall by freeing up valuable test instrument and technician time for performance of tests that are still relevant to patient outcomes.

If current test orders associated with the newly available data are still ideal 606, the system may make no change and wait 610 additional data before modifying or canceling any test orders. If current test orders are not ideal 606, the system may determine if they need to be modified 612 or canceled. In some cases, such as where new symptoms or newly available test results make an ordered test completely irrelevant 612, the system may simply cancel 614 the test order in order to prevent wasted time and materials. In other cases, modifying 616 the parameters of the test order may be sufficient to increase its value to the diagnoses. For example, in some situations a new test result or new piece of patient data may indicate that a white blood cell test of a blood sample is no longer relevant, but that a cholesterol count may now have some value to patient outcome. In such a case, the system may determine that the blood sample is already present at a location that has the capability of testing for cholesterol count and, instead of canceling the test altogether and causing the blood sample to be archived or disposed of and require a new sample, may instead modify 616 the test order to change the type of testing that is required.

III. Cross Discipline Test Result Management Case Studies

A variety of scenarios exist for which a cross disease management system, as described above, may improve the quality of treatment and patient outcomes by improving the efficiency of testing.

Diagnosis and Treatment of Depression

Lithium is widely used in the treatment of manic depressive psychosis. Administered as Lithium Carbonate, it is completely absorbed by the gastro-intestinal tract with peak serum levels occur 2 to 4 hours after an oral dose. The half life in serum is 48 to 72 hours and it is cleared through the kidneys (excretion parallels that of sodium). Reduced renal function can prolong clearance time. Lithium acts by enhancing the uptake of neurotransmitters which produces a sedative effect on the central nervous system. Serum Lithium concentrations are carried out essentially to ensure compliance and to avoid toxicity. Early symptoms of intoxication include apathy, sluggishness, drowsiness, lethargy, speech difficulties, irregular tremors, myoclonic twitchings, muscle weakness and ataxia. Levels higher than 1.5 mmol/L (12 hours after a dose) indicate a significant risk of intoxication.

Depression is a serious sickness that is an increasingly common diagnosis. Treatment of patients with depression has a high impact on healthcare systems and providers. Effective medication is available and extended in-patient treatment is uncommon, but the medication needs to be monitored very closely. If a patient is under medication for depression, the patient has a certain serum lithium level optimally around 1.2 to 1.5 mmol/l. Lithium level in serum is measured through ion-sensitive membranes. If the lithium level is below or above the reference range corridor of 1.2 to 1.5 mmol/l in serum it indicates that the patient is not following the medication guidance of the clinician or the chosen therapy (remedial measures) is not effective for this specific patient. If the volume is below the defined reference range during hospitalization the patient may be removed from the therapy (remedial measures), if the volume is above the range it may indicate that the patient is self medicating in some way or is having an unpredictable reaction to the therapy (remedial measures).

As therapeutic (remedial or medicinal) drug monitoring ("TDM") testing is costly and if the patient is below the reference range the outcome of the testing is "below cut-off"—the clinician can't gain any benefit from the laboratory result. In case the reference level is above it may indicate a need for urgent TDM testing because the patient is using other drugs on site or the dosage is too high. Treatment of that patient should be tightly controlled as it could be an indicator for an attempt at intentional overdosing.

Similarly, in situations where an unidentified young patient may come to the hospital due to an accident or alcohol misuse, they may be automatically tested for Lithium to check for drug abuse, as depression treatment drugs (e.g., amphetamines, analgesics) may be used as additive drugs for some recreational drugs (e.g., Ecstasy or MDMA), which may affect coagulation status. This testing may be required because TDM testing and measurement may not be a normal part of the night-shift test profile when such a patient may arrive, and the typically used night-shift test profiles, such as POCT testing, may not be reliable or sensitive enough to determine recreational drug use. Ecstasy has several known cooperative interactions with other drugs and can cause a serious and hazardous medical situation for a patient if not detected early on in treatment, which may lead to liability and waste for the clinician or hospital.

A middleware cross discipline management system as described above may be configured to execute certain test management rules to address the described situation. For example, one test management rule might cause an order for TDM testing to be automatically created where the test management data set indicates that a patient has previous test results that indicate past use of MDMA. Another test management rule might cause a test order to be created if TDM testing is required and lithium is missing. Another test management rule might cause a test order to be created based upon certain patient demographics and diagnosis present in the test management data set, such as a young patient exhibiting symptoms of alcohol misuse or intoxication. Another test management rule might cause a test order to be created if a patient has a history or other risk factors for drug misuse or overdosing in the test management data set. Other test management rules for addressing this use case will be apparent to one of ordinary skill in the art in light of the disclosure herein.

Creatinine Clearance Urine

Another use case for a cross discipline disease management system is the efficient testing and monitoring for characteristics of kidney failure, heart failure, and drug effects in drug abusing patients. A high confidence diagnosis of kidney malfunction or heart failure may require both urine samples and blood samples being collected from a patient at various intervals during treatment. The creatinine clearance test helps provide information about how well the kidneys are functioning. The test compares the creatinine level in urine with the creatinine level in blood. Creatinine is a chemical waste product of creatine, a chemical the body makes to supply energy to muscles. Comparing creatinine levels in urine with creatinine levels in blood provides an indication of glomerular filtration rate ("GFR"). GFR is a measure of how well the kidneys are functioning, especially the kidney's filtering function, which are called glomeruli.

Creatinine is removed or cleared from the body entirely by the kidneys. If kidney function is abnormal, creatinine level increases in the blood because less creatinine is released through the urine. Clearance is often measured as milliliters per minute (ml/min), with reference ranges in men of 97 to 137 ml/min and women of 88 to 128 ml/min. Creatinine in serum references ranges may vary from 0.6-1.2 mg/dl or 53.1-106.2 µmol/l in men, and 0.5-1.0 mg/dl or 44.3-88.2 µmol/l for women. Patients with a serum creatinine above 3 mg/dl could require continuous dialysis. Drug addicted or drug abusing patients may fake testing or diagnoses by diluting their samples by drinking extreme volumes of water in order to skew testing results lower.

A middleware cross discipline management system as described above may be configured to execute certain test management rules to address the described situation. For example, one test management rule may create test orders for creatinine clearance testing when the test management data set indicates that serum creatinine is above 3 mg/dl and patient history or diagnosis indicates kidney or heart disease. Another test management rule may create test orders for creatinine clearance testing as an add-on order if TDM testing is required. Other test management rules for addressing this use case will be apparent to one of ordinary skill in the art in light of the disclosure herein.

Sepsis Diagnosis

Another use case for a cross discipline disease management system is the efficient testing and monitoring for sepsis after surgery. During the wake up period after anesthesia patients are monitored very closely. Such monitoring includes non-invasive monitoring of pulse, temperature, and blood oxygenation. Based on the results of monitoring, the clinician may decide whether the patient should be in an intensive care unit or a normal care unit, or whether the patient may be discharged entirely. One early indicator of normal recovery is body temperature. If body temperature increases, the blood gas and blood count will be regularly checked including the erythrocyte sedimentation ratio (ESR) and the C-reactive protein (CRP) value. These parameters are pre-inflammation indicators which can identify a trauma reaction or a sepsis based on bacterial or viral inflammation. Since these parameters may have a slow response time to the conditions which cause them, for example, around 12 hours, result interpretation can be quite difficult.

Normal CRP ranges may be less than 10 mg/l, while levels of 10 to 50 mg/l indicate an infection with low or medium impact likely caused by a local infection or post-operative trauma, and levels of 50 to 100 mg/l indicate a high infection with a root cause analysis and immediate attention required. If CRP values increase quickly a clinician may not notice an increasingly dangerous risk of sepsis due to the slow response time. Based on a normal test result for a patient from an ICU department or post operation monitoring, a middleware cross discipline management system as described above may be configured to execute test management rules to monitor for measurements of interleukin-6 (IL-6) and procalcitonin test automatically as the values increase within short intervals of about 30 minutes to 2 hours to guide a clinician to avoid any delays for a necessary antibiotic therapy (analysis), or avoid a preventative but unnecessary and costly therapy (analysis) with antibiotics, which may lead to a better patient outcome.

IL-6 activates increasing leucocyte population in the blood count and can forewarn of an upcoming infection even before the fever of the patient is detected by the clinician. The test result of the IL-6 and procalcitonin tests may even allow a clinician to distinguish between a bacterial infection and an autoimmune reaction due to a chronic disease. For a clinician, this information is very important and would ideally be closely monitored by procalcitonin testing, since in the case of a bacterial inflammation the procalcitonin value increases while in the case of a viral infection the procalcitonin value is mostly in the normal range. Clinician monitoring of a patient with indication of an inflammation requires a blood sample to be collected for blood culture for a microbiologic testing before starting treatment with antibiotics. If procalcitonin in serum is increasing during monitoring, this indicates a bacterial infection.

Any bacterial infection requires further investigation due to the high risk of acquired hospitalization infection. Due to the risk, the clinician may have to perform regular microbiologic testing to distinguish between a hospitalization infection caused by multiple resistant *Staphylococcus aureus* ("MRSA") or by other bacteria. This provides an opportunity for a middleware system to be configured with a test management rule that aids in pre-surgery and post-surgery monitoring of IL-6 and procalcitonin for patient profiles as an early indication that can reduce the risk of undetected or misdiagnosed inflammation and can be very impactful for a better patient outcome by preventing or reducing unnecessary patient care and costs. Such a middleware system could be configured with test management rules for closely monitoring microbiologic testing and blood culture testing for bacterial growth, so that additional testing orders can be created as soon as possible from a multi antibiotic therapy (analysis) to a specific antibiotic therapy (analysis), reducing inefficient and unnecessary treatment.

Other potential indications of bacterial sepsis include Neutrophil and Monocyte volume. In some embodiments, a middleware system may include parameters indicating ranges of Neutrophil and/or Monocyte values which would be expected in patients who did not have bacterial sepsis (i.e., a patent with Neutrophil or Monocyte volumes within the specified ranges could confidently be treated as not having bacterial sepsis). In such embodiments, there may be a rule that, when a Neutrophil or Monocyte volume above the specified ranges was detected, the sample in which the out of range reading was detected could be routed to another analyzer for reflex testing to confirm or refute a potential diagnosis for bacterial sepsis. Additionally, in some embodiments, the range to be used in determining whether reflex testing should be applied may be tuned to context data regarding the relevant patient. For instance, in some cases if the patient was deemed to be at higher risk of sepsis (e.g., if he or she had recently undergone a surgical treatment), then a volume measurement that might otherwise be treated as normal could instead trigger reflex testing to identify potential bacterial sepsis. Other test management rules for addressing this use case will be apparent to one of ordinary skill in the art in light of the disclosure herein.

Erythrocyte Count

Another use case for a cross discipline disease management system is the efficient testing and monitoring of erythrocyte count, hemoglobin value, and mean corpuscular volume ("MCV") value measured in an EDTA blood ferritin serum. The erythrocytes contained in blood are responsible for gas exchange in our bodies through the lungs. The hemoglobin inside the erythrocytes are used as a carrier for oxygen into the body and $CO_2$ out of the body through the lungs. If the counted erythrocyte value is normal but the hemoglobin value is low the gas exchange capability through the lungs decreases. In response, the patient increases his ventilation ratio per minute to get enough oxygen into the body and $CO_2$ out of the body. If the oxygenation capability of the hemoglobin drops the patient may be centralized, meaning that blood circulation in the human body is limited to key functions and the blood is now only circulating between the brain and heart, with the peripheral body parts like the hands and legs not being supported.

Reference ranges for hemoglobin may be 12-15.5 g/dl for females and 14-15.5 g/dl for males. References ranges for erythrocyte may be 3.9-5.0 Mio/µl for females and 4.3-5.6 Mio/µl for males. References ranges of MCV may be about 84-98 fl. References ranges of mean corpuscular volume hemoglobin value per erythrocyte ("MCH") may be about 24-34 pg. References ranges for mean corpuscular hemoglobin volume may be about 32-36 g/dl. Multiple reasons can be related to a hemoglobin result outside of the reference ranges.

For example, low hemoglobin values can be indicated by interior bleeding or due to carcinoma in the human body. To distinguish between interior bleeding and a carcinoma the serum ferritin value can support the diagnostic pathway, as in the case of interior bleeding the serum ferritin is in the normal range and the erythropoietin (EPO) serum level is high due to increasing reticulocyte production in the bone marrow. Low hemoglobin result in combination with a low erythrocyte value can indicate interior bleeding, in this case the MCV value is in the normal range as calculated value and the serum ferritin level is normal as well, but the results of the blood coagulation (citrate tube) show abnormalities. A low hemoglobin result with a normal erythrocyte count end up in a low MCV value and can indicate that the patient is lacking vitamin B12, which gets measured in the serum. A re-run of the test may not help the clinician to take the action that is needed to improve patient outcomes.

A middleware cross discipline management system as described above may be configured to execute certain test management rules to address the described situation. For example, one test management rule may detect, based upon the data management set, information linked to a specific clinician, department, or diagnosis coding, or a patient previous result test, the need for additional blood testing and cause test orders to be automatically created in response. Another test management rule may cause test orders to be created based upon the test management data set containing patient demographics information, diagnosis and requester provided by a LIS, one or more of vitamin B12, EPO, or Ferritin results, or blood coagulation status. Other test management rules for addressing this use case will be apparent to one of ordinary skill in the art in light of the disclosure herein.

Further variations on, and features for, the inventors' technology will be immediately apparent to, and could be practiced without undue experimentation by, those of ordinary skill in the art in light of this disclosure. Accordingly, instead of limiting the protection accorded by this document, or by any document which is related to this document, to the material explicitly disclosed herein, the protection should be understood to be defined by the claims, if any, set forth herein or in the relevant related document when the terms in those claims which are listed below under the label "Explicit Definitions" are given the explicit definitions set forth therein, and the remaining terms are given their broadest reasonable interpretation as shown by a general purpose dictionary. To the extent that the interpretation which would be given to such claims based on the above disclosure is in any way narrower than the interpretation which would be given based on the "Explicit Definitions" and the broadest reasonable interpretation as provided by a general purpose dictionary, the interpretation provided by the "Explicit Definitions" and broadest reasonable interpretation as provided by a general purpose dictionary shall control, and the inconsistent usage of terms in the specification or priority documents shall have no effect.

Explicit Definitions

When appearing in the claims, a statement that something is "based on" something else should be understood to mean that something is determined at least in part by the thing that it is indicated as being "based on." When something is required to be completely determined by a thing, it will be described as being "based exclusively on" the thing.

When used in the claims, "configured" should be understood to mean that the thing "configured" is adapted, designed or modified for a specific purpose. An example of "configuring" in the context of computers is to provide a computer with specific data (which may include instructions) which can be used in performing the specific acts the computer is being "configured" to do. For example, installing Microsoft® WORD on a computer "configures" that computer to function as a word processor, which it does by using the instructions for Microsoft WORD in combination with other inputs, such as an operating system, and various peripherals (e.g., a keyboard, monitor, etc).

When used in the claims, "determining" should be understood to refer generating, selecting, defining, calculating or otherwise specifying something. For example, to obtain an output as the result of analysis would be an example of "determining" that output. As a second example, to choose a response from a list of possible responses would be a method of "determining" a response. As a third example, to identify data received from an external source (e.g., a microphone) as being a thing would be an example of "determining" the thing.

When used in the claims, a "set" should be understood to refer to a collection containing zero or more objects of the type that it refers to. So, for example, a "set of integers" describes an object configured to contain an integer value, which includes an object that contains multiple integer values, an object that contains only a single integer value, and an object that contains no integer value whatsoever.

The invention claimed is:

1. An information system for managing medical testing comprising:
   a. a computing server on a communication path between at least one laboratory instrument and at least one external patient data information system, the at least one external patient data information system configured to receive patient data from one or more sources other than through the computing server;
   b. an instrument communication interface communicatively coupled with the computing server and configured to provide a data communication between the computing server and the at least one external laboratory instrument;
   c. an information system interface communicatively coupled with the computing server and configured to provide a further data communication between the computing server and the at least one external patient data information system, wherein the at least one external patient data information system is configured to maintain a patient data set comprising a set of test orders and a history data set;
   wherein the computing server comprises:
      i. a first receiving section configured to receive an instrument data set from the at least one external laboratory instrument via the instrument communication interface;
      ii. a second receiving section configured to receive the history data set from the at least one external patient data information system via the information system interface;
      iii. a test management section configured to build a test management data set based on the instrument data set received from the at least one external laboratory instrument and based on the history data set received from the at least one external patient data information system;
      iv. a rules engine configured to apply a set of test management rules to the test management data set to generate a testing task; and
      v. an updating section configured to update a set of test orders of a patient data set maintained by the at least one external patient data information system based upon the testing task;
      wherein the instrument data set comprises test results associated with a patient; and
      wherein the history data set comprises at least one of biographical and historical information associated with the patient; and
      wherein the rules engine is configured to generate the testing task based upon a new piece of data in the test management data set, wherein the new piece of data in the test management data set is a result of a first test for the patient;
      wherein the testing task is a test order cancellation of a second test for the patient;
      wherein the rules engine is configured to determine whether to generate the test order cancellation based on whether the result of the first test for the patient renders the second test for the patient irrelevant; and
      wherein the rules engine is configured to generate the test order cancellation of the second test for the patient based on determining that the result of the first test for the patient renders the result of the second test for the patient irrelevant.

2. The system of claim 1, wherein the rules engine of the computing server is further configured to apply the set of test management rules to the test management data set in response to a change in the test management data set, wherein the change in the test management data set is associated with one or more of:
   a. a new patient diagnosis in the history data set;
   b. a change in the set of test orders;
   c. a change in the set of test management rules.

3. The system of claim 1, wherein the rules engine is configured to generate the testing task based upon a new piece of data in the test management data set; and
   wherein the set of test management rules comprises one or more rules configured to generate a new test order as the testing task, and one or more rules configured to generate a new sample and test order as the testing task.

4. The system of claim 1, wherein the rules engine is configured to generate the testing task based upon:
   a. a patient age;
   b. a patient identity; and
   c. a present medical condition of a patient; and
   wherein the set of test management rules comprises one or more rules configured to generate the testing task as remedial or medicinal drug monitoring.

5. The system of claim 1, wherein the set of test management rules comprises one or more rules configured to generate the testing task as creatinine clearance testing based upon:
   a. a serum creatinine level; and
   b. a past medical condition of the patient.

6. The system of claim 1, wherein the set of test management rules comprises one or more rules configured to generate the testing task as one or more of multi antibiotic analysis and specific antibiotic analysis based upon one or more of:
   a. microbiologic test results; and
   b. blood culture test results.

7. The system of claim 1, wherein the set of test management rules comprises one or more rules configured to generate the testing task as a blood ferritin serum test based upon one or more of:
   a. a medical diagnosis of the patient;
   b. a previous test result of the patient comprising one or more of B12, EPO, or Ferritin;
   c. a demographic information of a patient; and
   d. blood coagulation status.

8. The system of claim 1 further comprising an analytics component, wherein the analytics component is configured to receive a set of performance data from the computing server,
wherein the set of performance data comprises information describing an input and an output of the rules engine, and
wherein the analytics component is further configured to provide a modification to the rules engine based upon the set of performance data.

9. The system of claim 1, wherein the computing server is selected from the group consisting of:
a. a cloud based computing environment;
b. a dedicated server; and
c. a software process on a multi-function server.

10. A cross-discipline system for managing medical testing, the system comprising:
an information system for managing medical testing according to claim 1;
at least one laboratory instrument; and
at least one patient data information system configured to maintain a patient data set comprising a set of test orders and a history data set;
wherein the at least one laboratory instrument is communicatively coupled to the computing server of the information system via the instrument communication interface of the information system; and
wherein the at least one patient data information system is communicatively coupled to the computing server of the information system via the information system interface of the information system.

11. The system of claim 1, wherein the set of test management rules comprises one or more rules configured to generate the testing task as detecting sepsis or monitoring sepsis based upon on or more of:
a. a patient's temperature;
b. a patient's pulse;
c. a patient's blood oxygenation;
d. a previous test result of the patient comprising one or more of PCT, IL-6, CRP or ESR.

12. The system of claim 1, wherein the at least one external patient data information system comprises a laboratory information system (LIS).

13. The system of claim 12, wherein:
a. the LIS is a first LIS associated with a first laboratory;
b. the at least one external patient data information system comprises a second LIS associated with a second laboratory;
c. the at least one laboratory instrument comprises a first set of laboratory instruments associated with the first laboratory, and a second set of laboratory instruments associated with the second laboratory; and
d. the computing server is on a first communication path between the first LIS and the first set of laboratory instruments, and is on a second communication path between the second LIS and the second set of laboratory instruments.

14. The system of claim 1, wherein the at least one external patient data information system comprises a patient data information system operable to output information to a user other than through the computing server.

15. The system of claim 1, wherein:
a. the at least one external laboratory instrument comprises a plurality of external laboratory instruments;
b. the computing server comprises a processor programmed with instructions stored on a non-transitory computer readable medium to perform a set of acts comprising:
i. receiving, from the at least one external patient data information system one or more test requests associated with the patient;
ii. upon receiving the instrument data set comprising test rests associated with the patient from a first external laboratory instrument from the plurality of external laboratory instruments:
A. determining if additional test results associated with the patient are being generated by a second external laboratory instrument from the plurality of external laboratory instruments; and
B. updating the at least one external patient data information system with the test results associated with the patient and with the additional test results associated with the patients simultaneously by controlling updating with the test results based on generation of the additional test results.

16. The system of claim 1, wherein:
a. the instrument data set comprises instrument data not present at the at least one external patient data information system;
b. the at least one external laboratory instrument comprises a plurality of external laboratory instruments; and
c. the computing server comprises a processor programmed with instructions stored on a non-transitory computer readable medium to perform a set of acts comprising:
i. receiving, from the at least one external patient data information system one or more test requests associated with the patient; and
ii. based on the data not present at the at least one external patient data information system, allocating the one or more test requests associated with the patient among the plurality of external laboratory instruments.

17. The system of claim 1, wherein the computing server comprises a processor programmed with instructions stored on a non-transitory computer readable medium to perform a set of acts comprising:
a. upon receiving the instrument data set comprising test rests associated with the patient from the at least one external laboratory instrument, determining whether to generate an additional testing task by processing the test management data set comprising the test results associated with the patient; and
b. updating the at least one external patient data information system with the test results associated with the patient only after determining whether to generate the additional testing task.

18. The system of claim 1, wherein the computing server is configured to prioritize processing tasks by performing acts comprising:
a. applying the set of test management rules to new test results as the new test results are received from the at least one laboratory instrument; and
b. determining whether to generate test order cancellations only using processing resources not devoted to higher priority tasks as they become available.

19. A method for operating an information system for managing medical testing, the method comprising the steps of:

placing, on a communication path between an external patient data information system and at least one external laboratory instrument, a computing server, wherein, prior to placement of the computing server on the communication path, the external patient data information system was configured to communicate directly with the at least one external laboratory instrument;

receiving, with the computing server, an instrument data set from the at least one external laboratory instrument via a instrument communication interface;

receiving, with the computing server, a history data set from the external patient data information system via an information system interface;

building, with the computing server, a test management data set based on the received instrument data set and based on the received history data set;

generating, with the computing server, a testing task based on applying a set of test management rules to the test management data set; and updating, with the computing server, a set of test orders of a patient data set maintained by the external patient data information system based on the generated testing task;

wherein the instrument data set comprises test results associated with a patient;

wherein the history data set comprises at least one of biographical and historical information associated with the patient;

wherein the testing task is a test order cancellation of a second test for the patient generated based upon a new test result of a first test for the patient in the test management data set;

wherein the set of test management rules comprises one or more rules indicating that the result of the first test for the patient renders the result of the second test for the patient irrelevant.

20. The method of claim 19, wherein the set of test management rules comprises one or more rules configured to generate the testing task as performing a test on the sample, wherein the test to be performed on the sample is a test for one or more inflammation marker, said inflammation marker being selected from the group consisting of ESR, CRP, IL-6 and PCT.

* * * * *